United States Patent
Sherman et al.

(10) Patent No.: US 11,832,803 B2
(45) Date of Patent: *Dec. 5, 2023

(54) SPECIMEN RETRIEVAL SYSTEM FOR USE IN ENDOSCOPIC SURGERY

(71) Applicant: Freehold Surgical, LLC, New Hope, PA (US)

(72) Inventors: Darren R. Sherman, New Hope, PA (US); Jeffrey Smith, New Hope, PA (US)

(73) Assignee: Freehold Surgical, LLC, New Hope, PA (US)

( * ) Notice: Subject to any disclaimer, the term of this patent is extended or adjusted under 35 U.S.C. 154(b) by 293 days.

This patent is subject to a terminal disclaimer.

(21) Appl. No.: 17/094,633

(22) Filed: Nov. 10, 2020

(65) Prior Publication Data
US 2021/0052262 A1 Feb. 25, 2021

Related U.S. Application Data

(63) Continuation of application No. 16/094,708, filed as application No. PCT/US2017/028375 on Apr. 19, 2017, now Pat. No. 10,835,219.
(Continued)

(51) Int. Cl.
*A61B 17/00* (2006.01)
*A61B 10/04* (2006.01)
(Continued)

(52) U.S. Cl.
CPC ........ *A61B 17/00234* (2013.01); *A61B 10/04* (2013.01); *A61B 10/06* (2013.01);
(Continued)

(58) Field of Classification Search
CPC ........ A61B 17/00234; A61B 17/22031; A61B 17/221; A61B 2017/00287;
(Continued)

(56) References Cited

U.S. PATENT DOCUMENTS 5,176,687 A * 1/1993 Hasson ................ A61B 17/221
606/127
5,524,633 A * 6/1996 Heaven .............. A61B 17/0218
600/562

(Continued)

FOREIGN PATENT DOCUMENTS

CN 2643842 9/2004
CN 102138811 8/2011
(Continued)

OTHER PUBLICATIONS

Office Action from Chinese Patent Application No. 201780037810.6 dated Nov. 4, 2020.
(Continued)

*Primary Examiner* — Sarah A Long
(74) *Attorney, Agent, or Firm* — CROCKETT & CROCKETT, PC; K. David Crockett, Esq.

(57) ABSTRACT

A specimen retrieval system for easier tissue removal during endoscopic surgery. The device includes a specimen tube with a main tube, and a mechanism for pulling and everting the distal end of the tube into the tube, or a side channel provided within the tube. The mechanism may include a tether fixed to the distal edge of the tube, or a grasper operable to grasp the distal edge of the tube.

21 Claims, 35 Drawing Sheets

Related U.S. Application Data

(60) Provisional application No. 62/375,055, filed on Aug. 15, 2016, provisional application No. 62/324,802, filed on Apr. 19, 2016.

(51) Int. Cl.
  *A61B 10/06* (2006.01)
  *A61B 17/22* (2006.01)
  *A61B 17/221* (2006.01)

(52) U.S. Cl.
  CPC ...... *A61B 17/221* (2013.01); *A61B 17/22031* (2013.01); *A61B 2017/00287* (2013.01); *A61B 2017/00557* (2013.01); *A61B 2017/00818* (2013.01); *A61B 2017/2215* (2013.01); *A61B 2017/22072* (2013.01)

(58) Field of Classification Search
  CPC .......... A61B 2017/00557; A61B 2017/00818; A61B 2017/22072; A61B 2017/2215; A61B 10/04
  See application file for complete search history.

(56) References Cited

U.S. PATENT DOCUMENTS

| | | |
|---|---|---|
| 6,527,748 B1 | 3/2003 | Suzuki |
| 6,971,988 B2 | 12/2005 | Orban, III |
| 2004/0242960 A1 | 12/2004 | Oban, III |
| 2005/0288652 A1 | 12/2005 | Suzuki |
| 2008/0103508 A1* | 5/2008 | Karakurum ...... A61B 17/00234 606/127 |
| 2010/0016792 A1 | 1/2010 | Hirszowicz |
| 2011/0087235 A1 | 4/2011 | Taylor et al. |
| 2011/0184432 A1 | 7/2011 | Parihar et al. |
| 2012/0238823 A1 | 9/2012 | Hagerty et al. |
| 2012/0283760 A1 | 11/2012 | Sepetka et al. |
| 2013/0231677 A1* | 9/2013 | Carroux ................. A61B 1/307 606/127 |
| 2015/0320409 A1* | 11/2015 | Lehmann ............. A61B 17/221 600/109 |

FOREIGN PATENT DOCUMENTS

| | | |
|---|---|---|
| JP | 2007082675 | 4/2007 |
| WO | WO0191652 | 12/2001 |
| WO | WO2015084769 | 6/2015 |
| WO | WO2016028789 | 2/2016 |

OTHER PUBLICATIONS

International Preliminary Report on Patentability from IA PCT/US2017/028375 dated Mar. 27, 2018.
Extended European Search Reported from European Patent Application No. 17786557.3 dated Apr. 2, 2019.
Extended European Search Report dated Dec. 6, 2021 from European Patent Application No. 21191226.6.

* cited by examiner

SPECIMEN RETRIEVAL SYSTEM FOR USE IN ENDOSCOPIC SURGERY

This application is a continuation of U.S. application Ser. No. 16/094,708, filed Oct. 18, 2018, now U.S. Pat. No. 10,835,219, which is a national stage of International Application PCT/US2017/028375, filed Apr. 19, 2017, which claims priority to U.S. Provisional Application 62/375,055, filed Aug. 15, 2016, and U.S. Provisional Application 62/324,802, filed Apr. 19, 2016.

FIELD OF THE INVENTIONS

The inventions described below relate the field of specimen collection during endoscopic surgery.

BACKGROUND OF THE INVENTIONS

Endoscopic surgery is often used to remove diseased tissue from the abdomen. During endoscopic surgery of the abdomen, a surgical team inflates the abdomen to create a surgical workspace, and inserts surgical instruments and an endoscope into the abdomen through several portals cut through the abdominal wall. In surgeries such as gall bladder removal, tumor removal, and appendectomy, a surgeon will cut tissue from surrounding tissue and remove that tissue from the workspace. In many cases, it is best to quickly isolate the excised tissue from the remaining tissue in the workspace, because the tissue may be infected or cancerous. To isolate the tissue and make it easier to remove it, a surgeon will often insert a specimen bag into the workspace, place the tissue in the specimen bag, and pull the specimen from the workspace through one of the portals used to perform the surgery.

Current specimen bags used in endoscopic surgery are mere plastic bags or bags supported by hoops (like fishing nets). Bert™ tissue retrieval bags are unstructured floppy bags. A surgeon will drop the bag into the surgical workspace, open the bag with a grasper operated through a first portal and fill the bag with a grasper inserted through a second portal, while using an endoscope inserted through a third portal to visualize the procedure. Ethicon's Endo-Pouch® specimen retrieval bag resembles a fishing net with a collapsible hoop. The EndoPouch® specimen retrieval bag is inserted through a cannula in a first portal, and is self-opening. A surgeon must use a grasper inserted through a second portal to grab tissue and drop the tissue into the bag, and must insert an endoscope through a third portal to visualize the procedure.

SUMMARY

The specimen retrieval systems and methods described below provide for easier tissue removal during endoscopic surgery of the abdomen, and reduces the number of portals needed to retrieve tissue. The specimen retrieval systems include a specimen tube assembly comprising a main tube a tether secured to the distal end of the tube and extending proximally through the tube and beyond the proximal end of the tube. The specimen retrieval systems may also include the specimen tube assembly comprising the main tube with a side channel tube, a hoop in the distal end of the main tube, with the tether secured to the hoop and extending through the side channel and out of the proximal end of the specimen tube. With the distal end of the specimen tube disposed in the abdomen of a patient, the hoop and the distal edge of the main tube can be pulled into the side channel, until a portion of the tube is everted into the side channel. When the distal edge of the tube is pulled into the proximal portion of the tube, and resides outside the patient's abdomen, the surgeon can pull the specimen tube assembly from the abdomen. Any tissue or fluid in the specimen tube assembly is isolated from the workspace because the specimen tube assembly, in its everted configuration, is closed to the workspace. Any tissue or fluid in the specimen which might by deposited on the outside of the tube distal end, or the edge of the tube, is also isolated from the workspace upon eversion of the distal end of the tube into the remainder of the tube.

While the use of the specimen tube assembly is described below in reference to abdominal endoscopic surgery, the specimen tube assembly and its method of use may be used to retrieve tissue or objects from any surgical or natural workspace of the body.

DETAILED DESCRIPTION OF THE INVENTIONS

Figure 1:
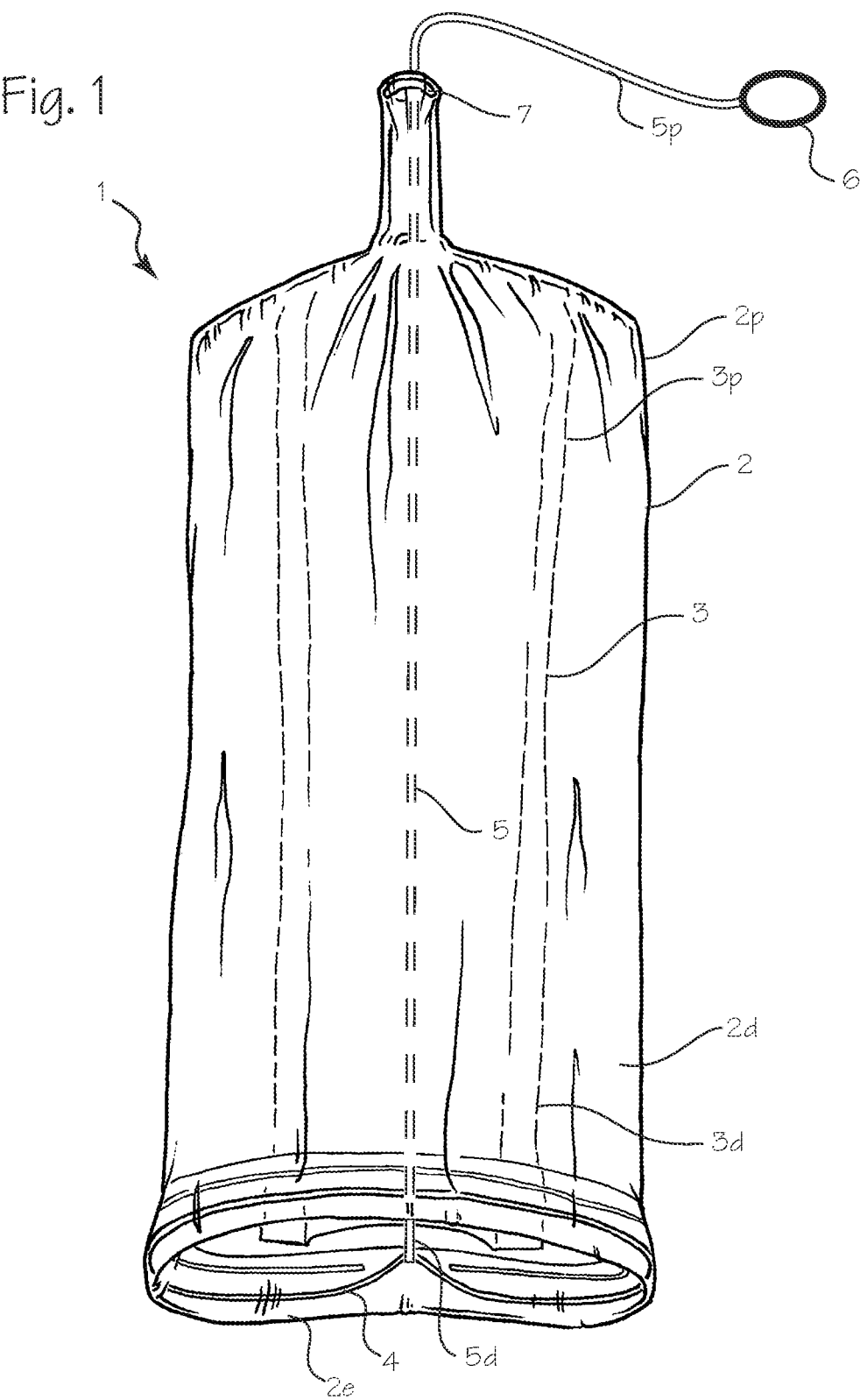
FIG. 1 illustrates a specimen tube assembly operable to partially evert to provide an enclosure for specimens obtained in a surgical workspace.

FIG. 1 illustrates a specimen tube assembly operable to partially evert to provide an enclosure for specimens obtained in a surgical workspace. As shown in FIG. 1, the specimen tube assembly 1 comprises a main tube 2, with a distal end 2d and a proximal end 2p, and a side channel tube 3, secured within the main tube, with a distal end 3d terminating near the distal end 2d of the main tube (preferably a short distance proximal to the distal edge 2e of the main tube), and a proximal end 3p terminating proximate the proximal end 2p of the main tube. A semi-rigid or resilient hoop 4 is secured to the distal end of the tube, circumscribing the opening at the distal end. The hoop may be captured in a hem formed by doubling or turning over the edge of the tube on itself and securing it to the tube to create a channel in which the hoop resides, or the hoop may be glued or melted to the tube, or the hoop may be integrally formed with the tube. The hoop may be a complete or partial ring. Preferably, the hoop 4 is semi-rigid, with sufficient hoop strength to open the distal end of the tube when unconstrained, and, preferably, a hoop strength greater that the hoop strength of the tube 2. A tether 5 is disposed within the side channel 3, extending from beyond the distal end of the side channel to the proximal end of the side channel and beyond. The tether may be discrete or integrally formed with the hoop. (The loop and tether may be also formed as a lasso, with an eye of the lasso located where the joint between the hoop and the tether is depicted, and the lasso loop corresponding to the hoop and the lasso spoke corresponding the tether.) At the distal end 5d of the tether, the tether is secured to the hoop 4. The proximal end 5p of the tether extends proximally to the proximal end of the side channel and the main tube, and proximally out of the proximal end of both the side channel and the main tube. A pull ring 6 may be attached to the proximal end of the tether. An additional ring 7 may be disposed at the proximal end or edge of the main tube. This additional ring is preferably rigid or semi-rigid, to hold the proximal end open as needed to accommodate laparoscopic instruments. As illustrated, the proximal end 2p of the main tube is funnel-shaped, with a small diameter segment relative to the distal end of the main tube. However, the main tube distal and proximal openings may be roughly the same size.

Figure 3:
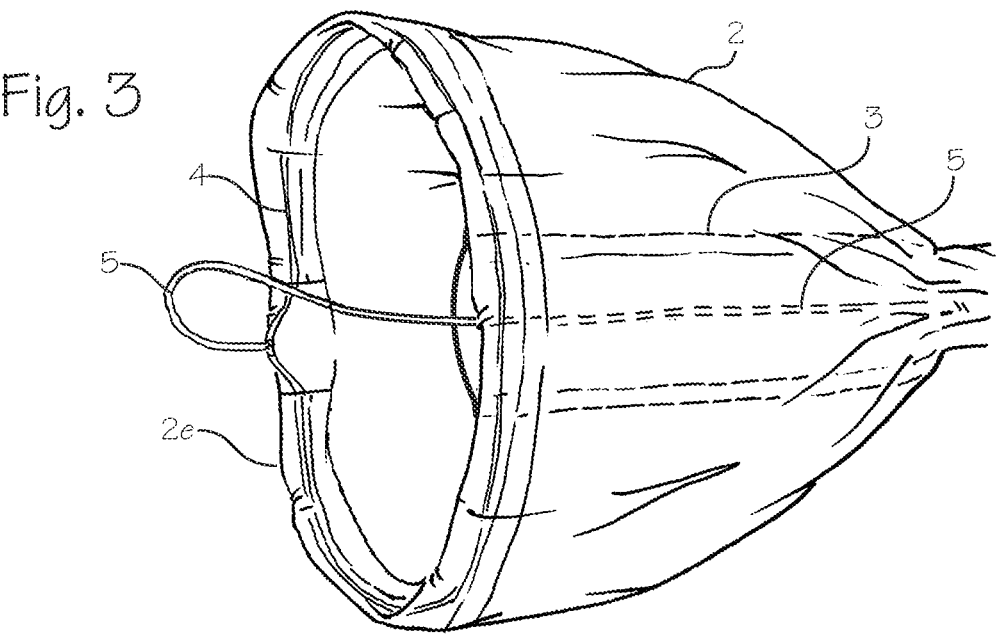
FIG. 3 is a detail of the distal end of the tube, illustrating an arrangement of the hoop and tether.
Figure 2:
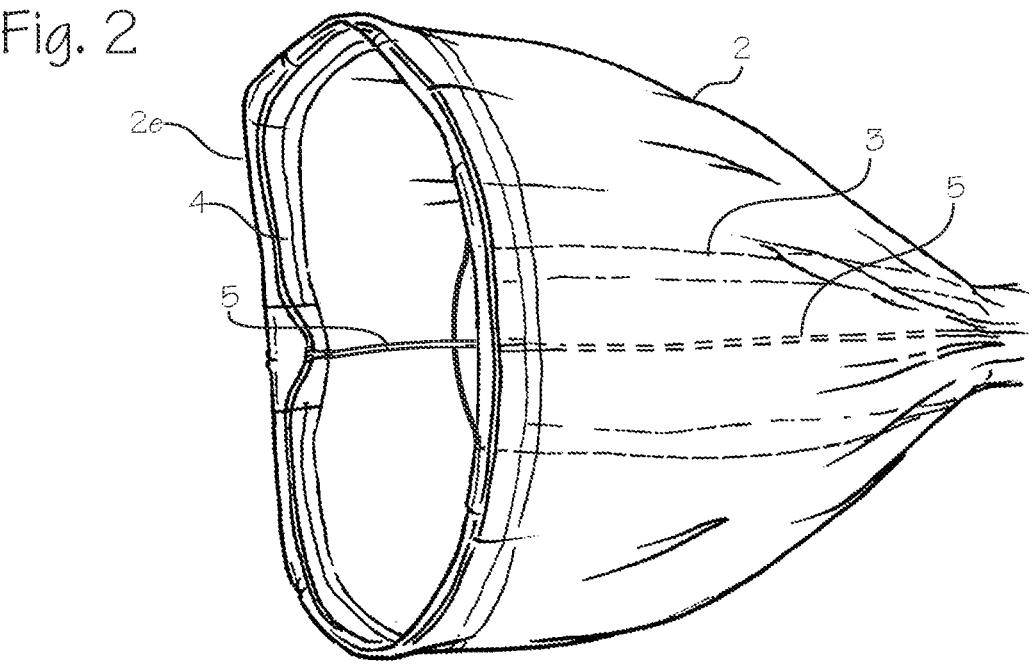
FIG. 2 is a detail of the distal end of the tube, illustrating an arrangement of the hoop and tether.
Figure 4:
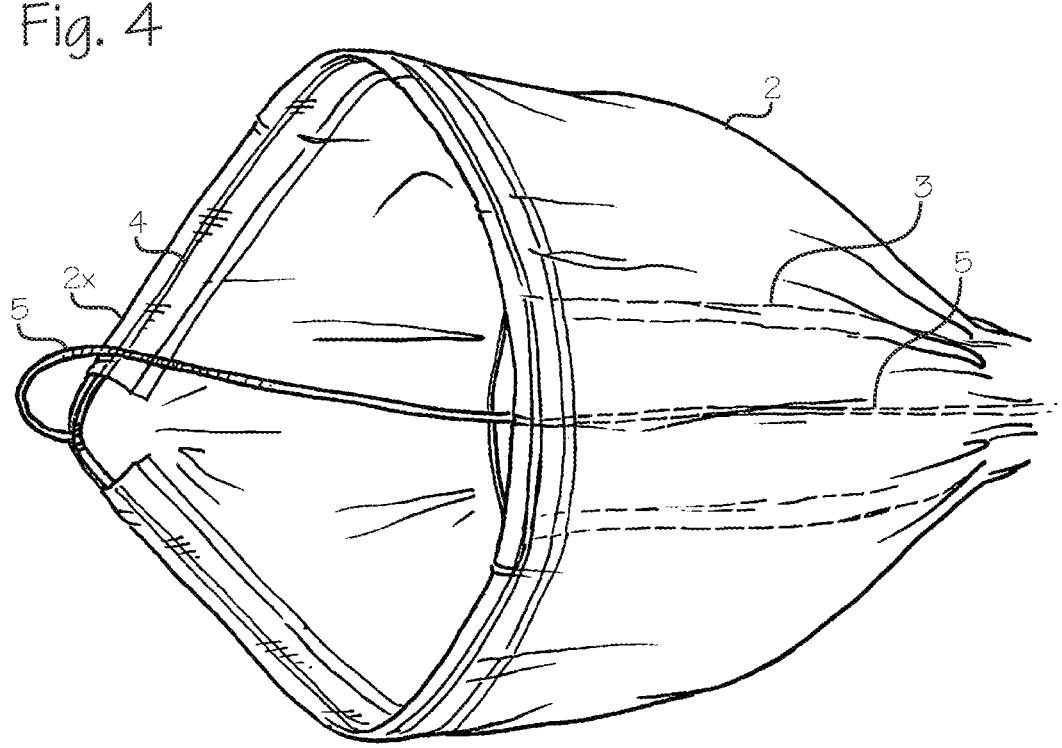
FIG. 4 is a detail of the distal end of the tube, illustrating an arrangement of the hoop and tether.

FIGS. 2, 3 and 4 illustrate versions of the distal edge of the tube. As shown in FIG. 2, the distal end may be square cut, with the tether secured to the hoop at a point within an arcuate region of the hoop radially proximate the side channel 3. In FIG. 2, the arcuate portion of the hoop at which the tether is attached is biased to curve slightly proximally, to facilitate entry of the hoop 4 into the side channel. As shown in FIG. 3, the distal end may be square cut, with the tether secured to the hoop at a point within an arcuate region of the hoop radially spaced, preferably radially opposite, the side channel. In FIG. 3, the arcuate portion of the hoop at which the tether is attached is curved slightly distally, to facilitate entry of the hoop into the side channel on the opposite side of the main tube. As shown in FIG. 4, the main tube distal end 2 is bevel-cut, with a pointed distally extending portion 2x radially opposite the side channel, and the tether secured to the hoop at a point proximate the pointed region, preferably at the point. The tether in this illustration is secured to the hoop at a point within an arcuate region of the hoop radially spaced, preferably radially opposite, the side channel.

Figure 5:
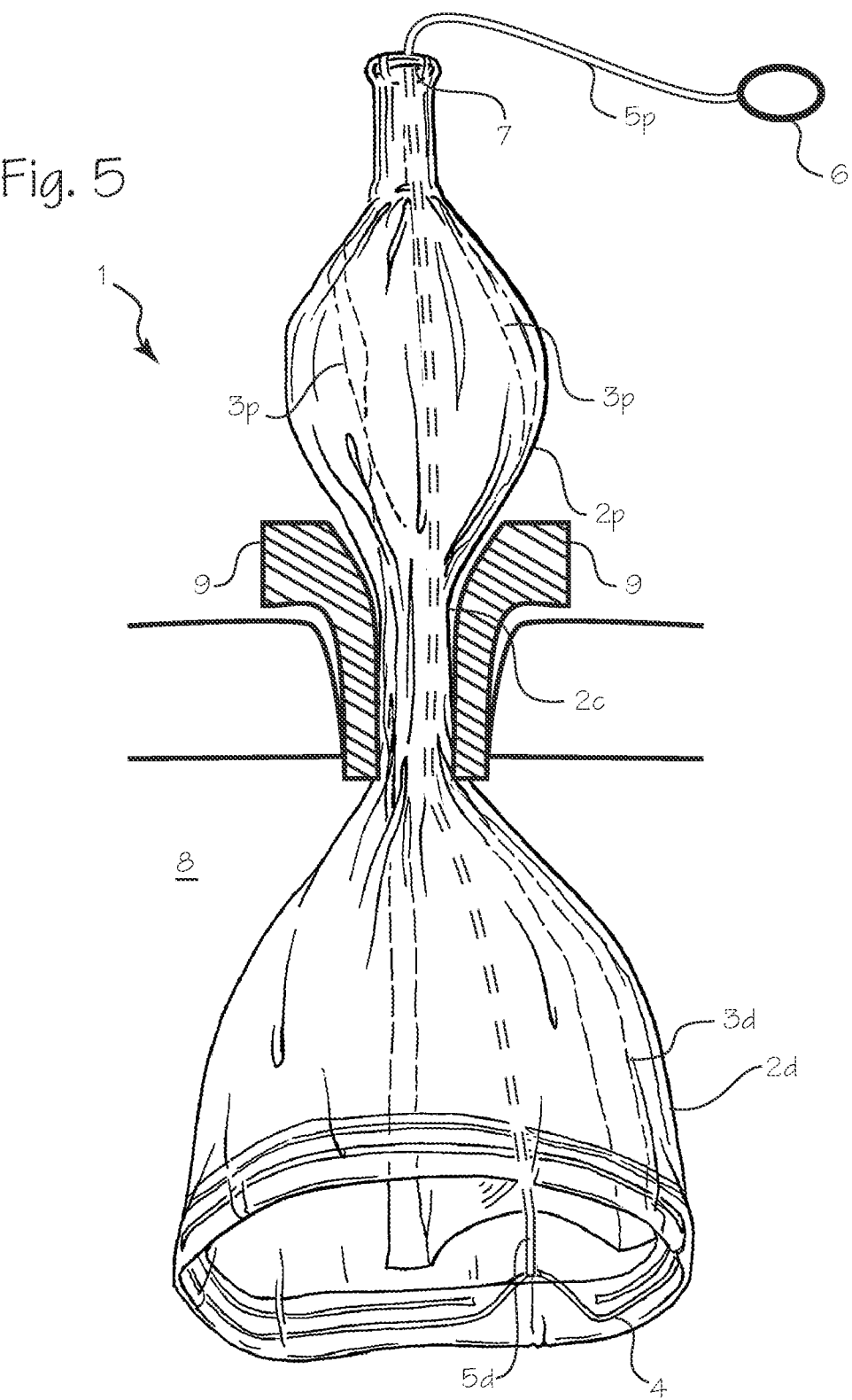
FIG. 5 is a view of the specimen tube assembly, illustrating placement of the device in a surgical workspace.

The use of the specimen tube assembly is explained in FIGS. 5 through 11. A user, such as a surgeon, will perform each step to isolate and remove a portion of body tissue that has been dissected from surrounding tissue. As shown in FIG. 5, a surgeon has inserted the specimen tube assembly 1 into the surgical workspace 8 through a cannula or portal 9 which has been placed in an incision in the skin overlying the surgical workspace, such that the distal end 2d of the main tube is disposed in the workspace 8, the proximal end 2p of the main tube is disposed outside the body of the patient, with a central portion 2c disposed in the cannula/portal. The hoop 4 is sufficiently resilient to hold the distal end of the main tube open when unconstrained. The tether proximal end 5p and pull ring 6 remain outside the body. Placement of the distal end of the specimen tube assembly may be observed with an endoscopic camera, inserted into the surgical workspace through a second portal.

Figure 6:
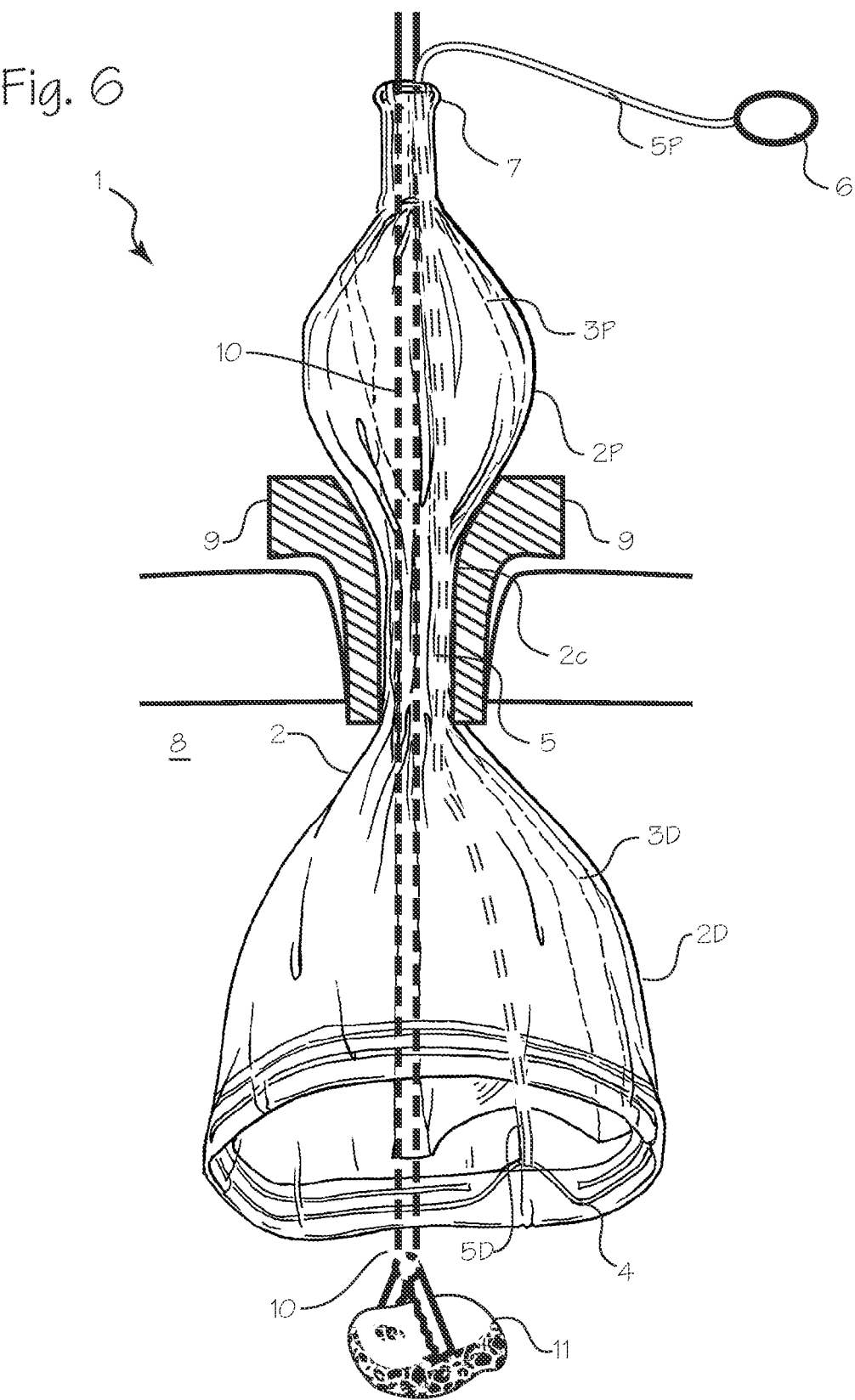
FIG. 6 is a view of the specimen tube assembly, illustrating insertion of a grasper, through the specimen tube assembly proximal end and into the workspace.
Figure 7:
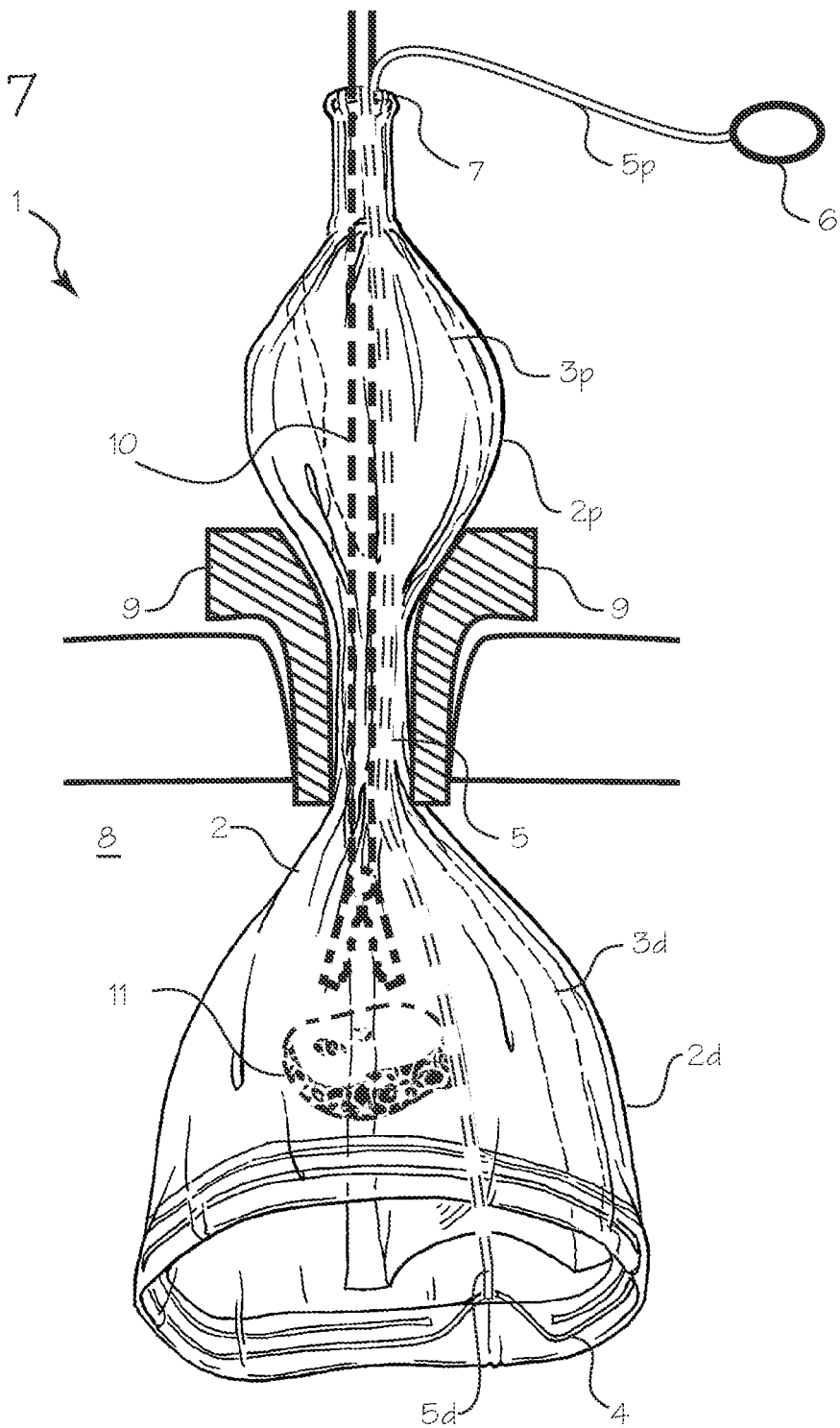
FIG. 7 is a view of the specimen tube assembly, illustrating drawback of the grasper to place a piece of tissue from the workspace into the specimen tube assembly.

As shown in FIG. 6, the surgeon inserts a grasper 10 into the bag, from the proximal end, to position the grasping jaws of the grasper in the workspace. The surgeon then grasps the body tissue, item 11, and pulls it into the main tube, as shown in FIG. 7. The surgeon may then withdraw the grasper completely from the specimen tube assembly, or may leave the grasper in place, with the tip of the grasper within the distal portion of the bag, to be used as a rigid element to facilitate eversion in the next steps. The grasper is preferably freely movable within the tube, but it may be secured to the proximal end of the tube by the additional ring 7, using an elastic ring, or by fixing the ring to the grasper with adhesive.

Figure 8:
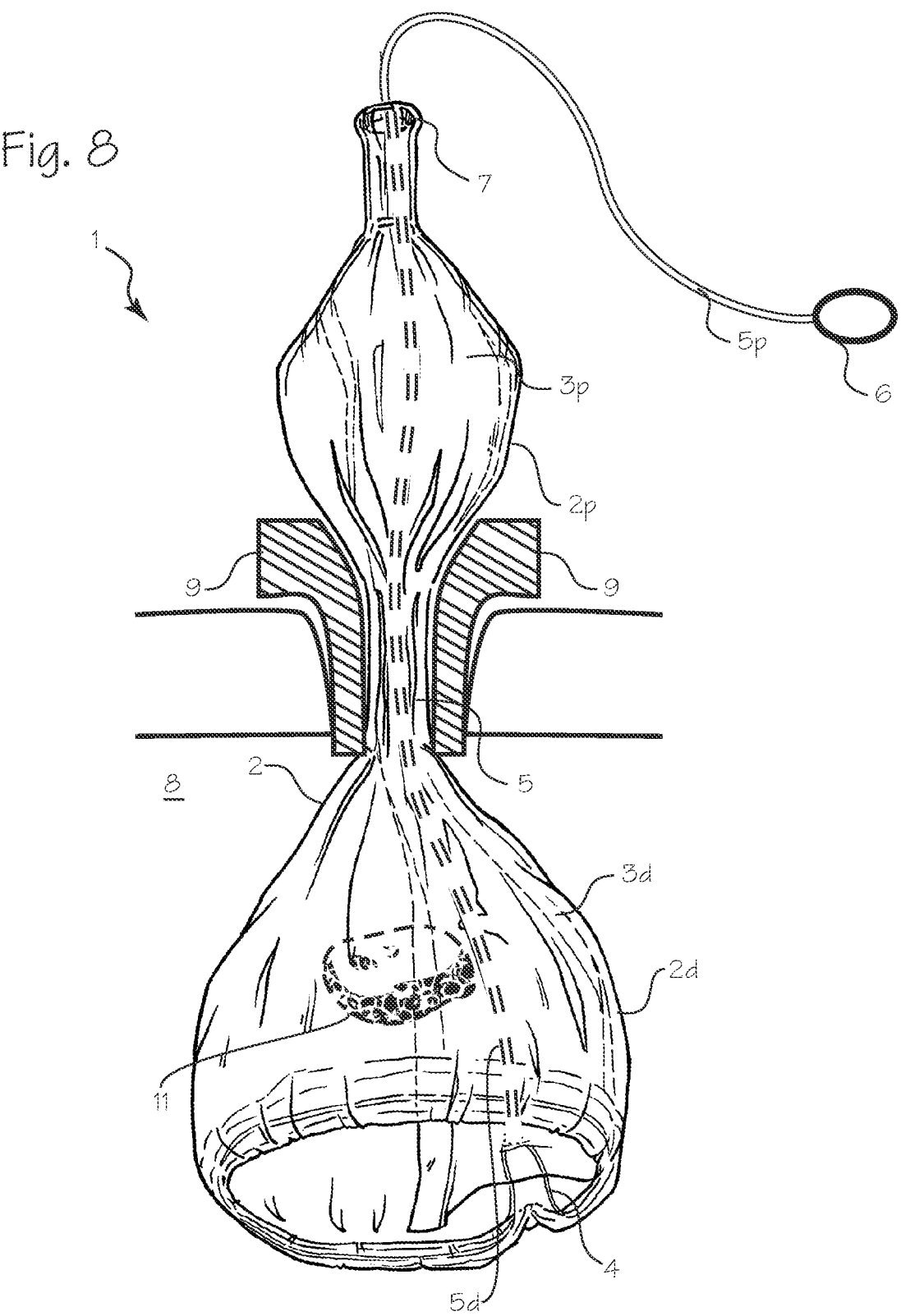
FIG. 8 is a view of the specimen tube assembly, illustrating initial pullback of the tether, to draw the hoop into the side channel.
Figure 9:
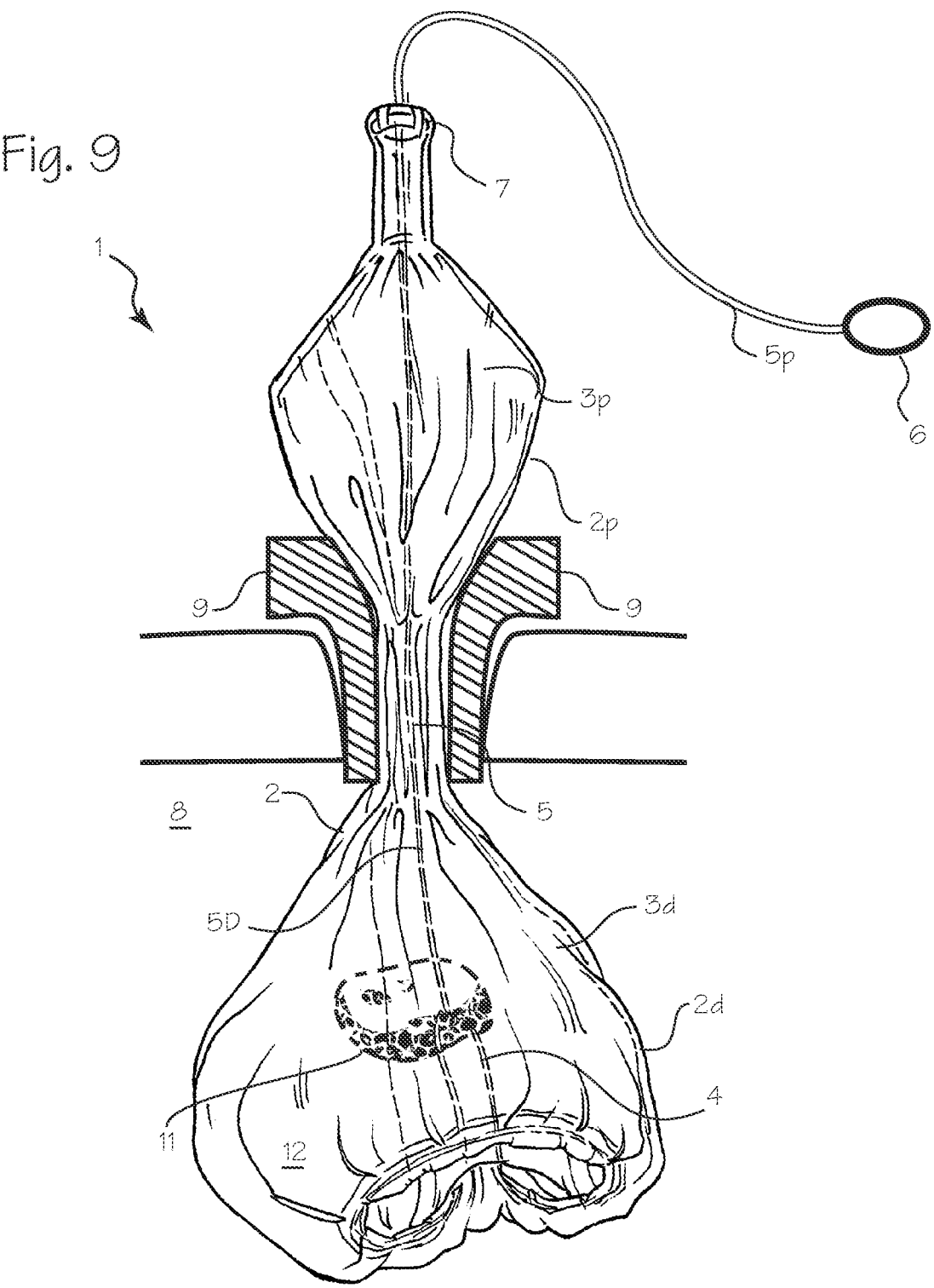
FIG. 9 is a view of the specimen tube assembly, illustrating a further pullback of the tether to draw the hoop proximally within the side channel and draw the open distal end of the tube into the side channel.

As shown in FIG. 8, the surgeon pulls the tether proximally, using the proximal portions 5p of the tether (and the pull ring 6, if provided), to draw the hoop into the side channel. FIG. 8 shows the hoop just entering the side channel, while FIG. 9 shows the device with the hoop drawn almost entirely into the side channel, such that the open edge of the main tube is almost entirely located within the side channel and the body tissue. When the hoop 4 is entirely within the side channel, it is isolated from the workspace by the remaining exposed side wall 12 of the main tube. The eversion which occurs in these steps may be facilitated with the grasper, holding the grasper in place in the main tube distal end to provide a rigid post over which the main tube material can slide while everting. The grasper may also be used to hold the side channel in place during eversion of the distal portion of main tube into the side channel. However, as illustrated, the grasper is not necessary to accomplish the method.

Figure 10:
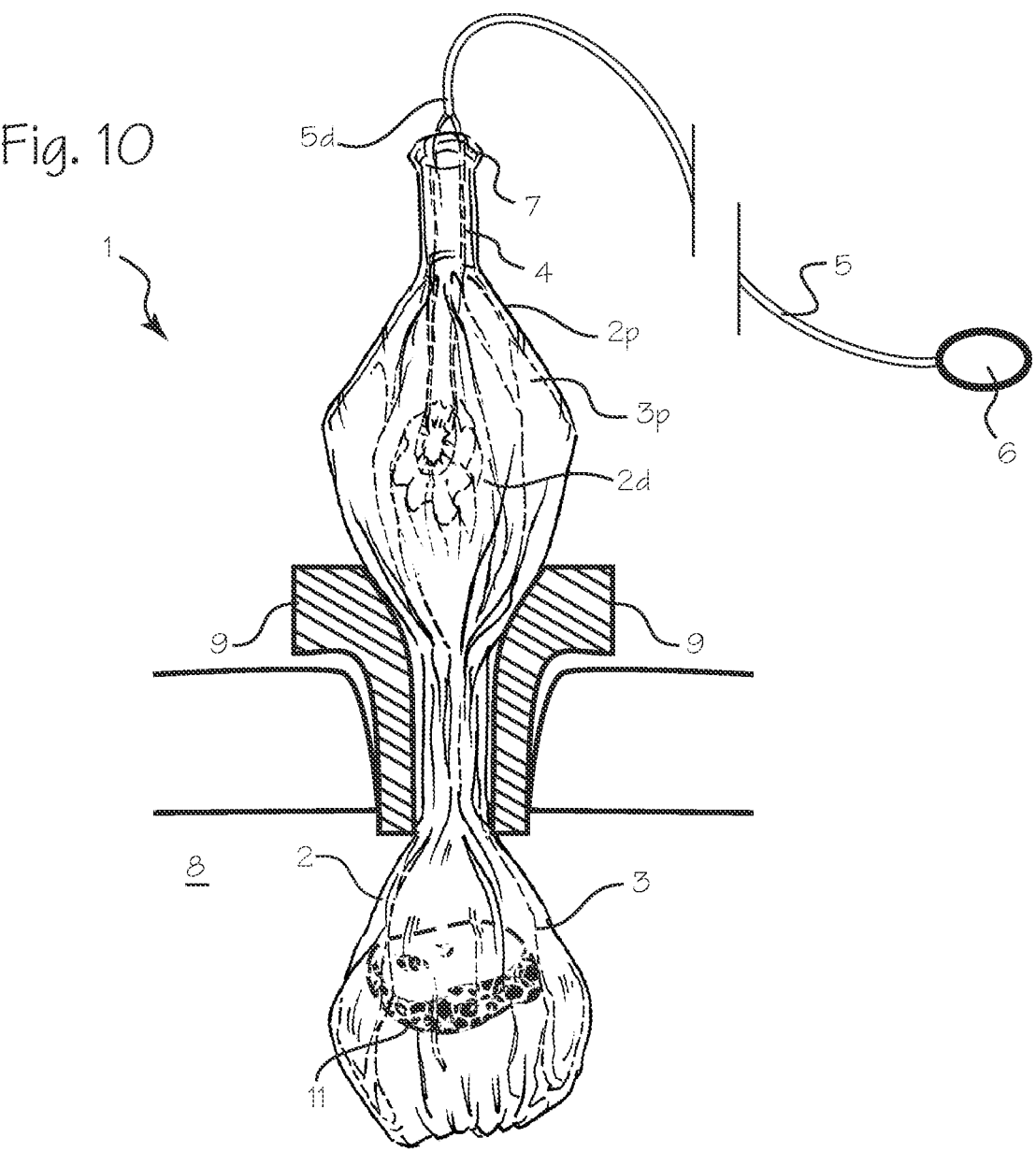
FIG. 10 is a view of the specimen tube assembly, illustrating a further pullback of the tether to draw the hoop proximally within the side channel to reside outside the workspace.
Figure 11:
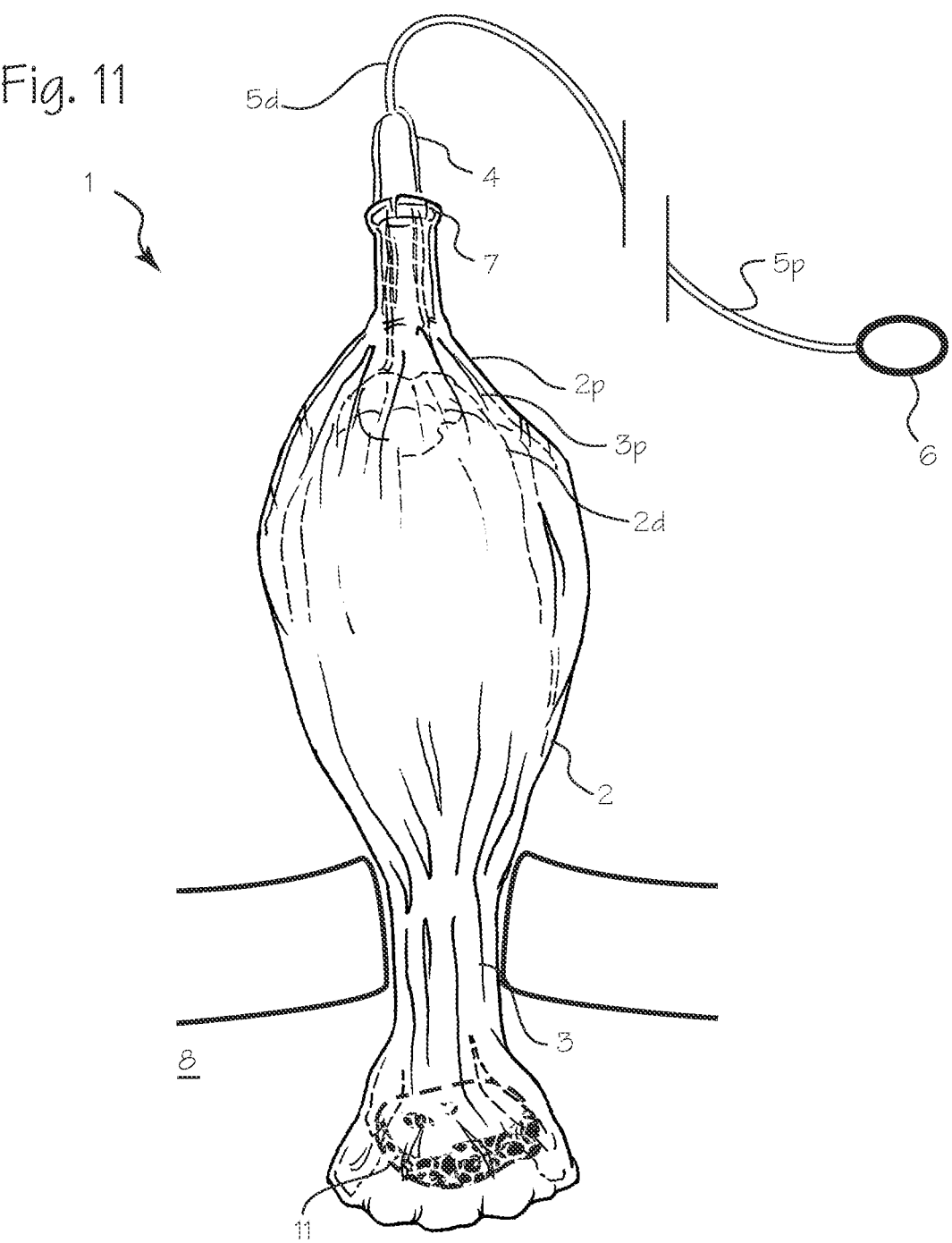
FIG. 11 illustrates withdrawal of the specimen tube assembly from the workspace.

In FIG. 10, the surgeon has pulled the tether 5 and hoop 4 proximally within the side channel, until the hoop 4 and distal end 2d of the main tube are located entirely outside the body. At this point, any fluids or diseased cells that leak from the distal end of the main tube will spill outside the workspace. Finally, the surgeon will pull the entire specimen tube assembly out of the workspace. Finally, as shown in FIG. 11, entire tube, in its everted configuration, with the portion of body tissue contained within the everted tube, can be pulled from the workspace through the incision. The everted distal end of the bag, and the proximal end of the bag, may be tied closed before withdrawal, and the cannula may be withdrawn with the bag or it may be withdrawn before pulling the bag from the workspace.

Figure 12:
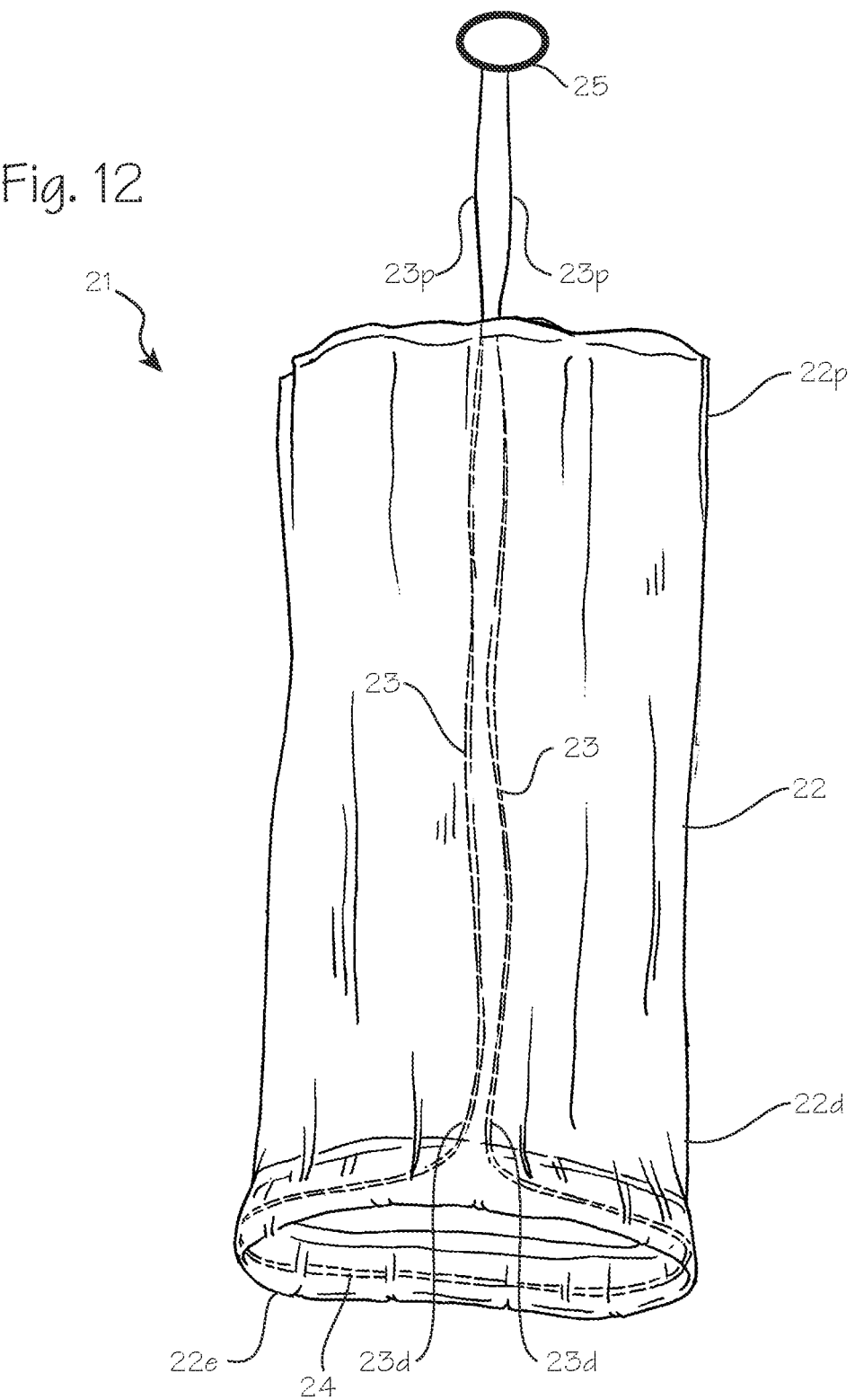
FIG. 12 illustrates a simple version of an everting specimen tube assembly with a tether.

FIG. 12 illustrates a simple version of an everting specimen tube assembly with a tether. In this embodiment, the specimen tube assembly 21 comprises a tube 22 with a distal end 22d and a proximal end 22p with a tether 23 with a distal end 23d and a proximal end 23p. The tether is secured to the distal edge 22e of the specimen tube assembly tube 22, optionally to a hoop 24. The tether runs proximally through the tube 22 (no side tube is used in this embodiment), to extend out the proximal opening of the tube 22. The hoop 24 and tether 23 can be formed integrally or separately, and one or both can be semi-rigid and resilient, like a collapsible O-ring, or limp and non-elastic, like nylon thread or suture. Preferably, the hoop 24 is semi-rigid, with sufficient hoop strength to open the distal end of the tube when unconstrained, and, preferably, a hoop strength greater that the hoop strength of the tube 22. As with the previous embodiment, the ring disposed at the distal end of the tube can be hemmed into the distal end, glued to the distal end, melted to the distal end, or formed integrally with the distal end. A pull ring 25 may be attached to the proximal end of the tether. As appears from comparison of FIGS. 1 and 12, the hoops 4 and 24 and their corresponding tethers may interchanged and used with the various embodiments depicted in the drawings.

Figure 13:
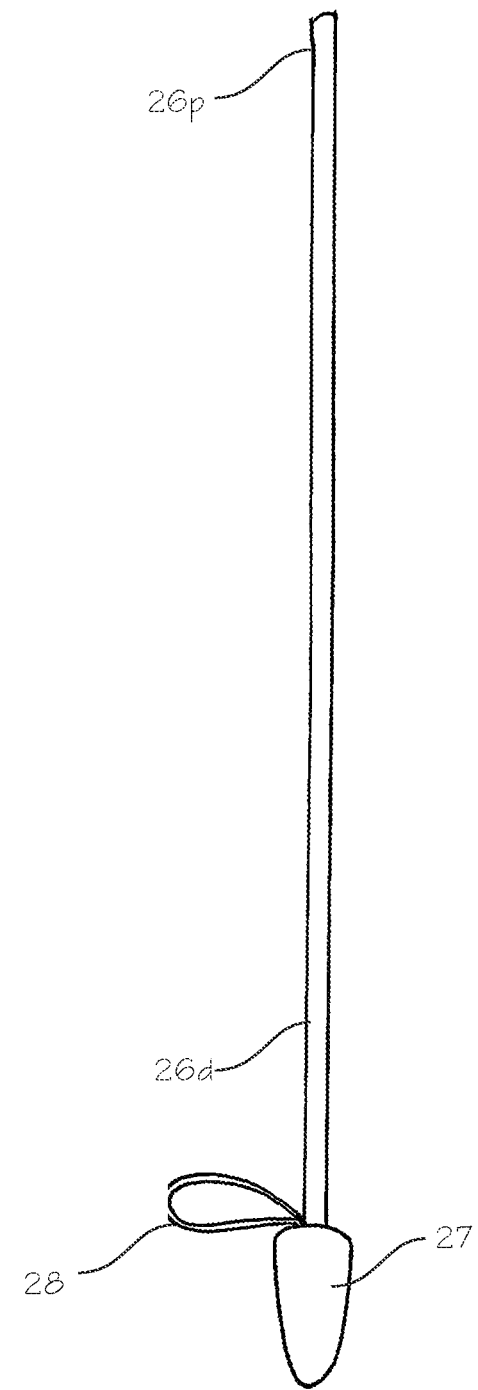
FIG. 13 illustrates a stick for use with the everting specimen tube assembly of FIG. 12.

FIG. 13 illustrates a rod for use with the everting specimen tube assembly of FIG. 12. The rod 26 has blunt rounded distal tip 27, and a second, semi-rigid guide ring 28 located on near the distal end 26d of the rod. The proximal end 26p of the stick extends out of the proximal end of the bag 22. The guide ring is preferable resiliently deformable, so that it may be compressed to a small configuration to fit through a portal and expand once release from the portal inside the workspace, as shown in the following figures.

Figure 14:
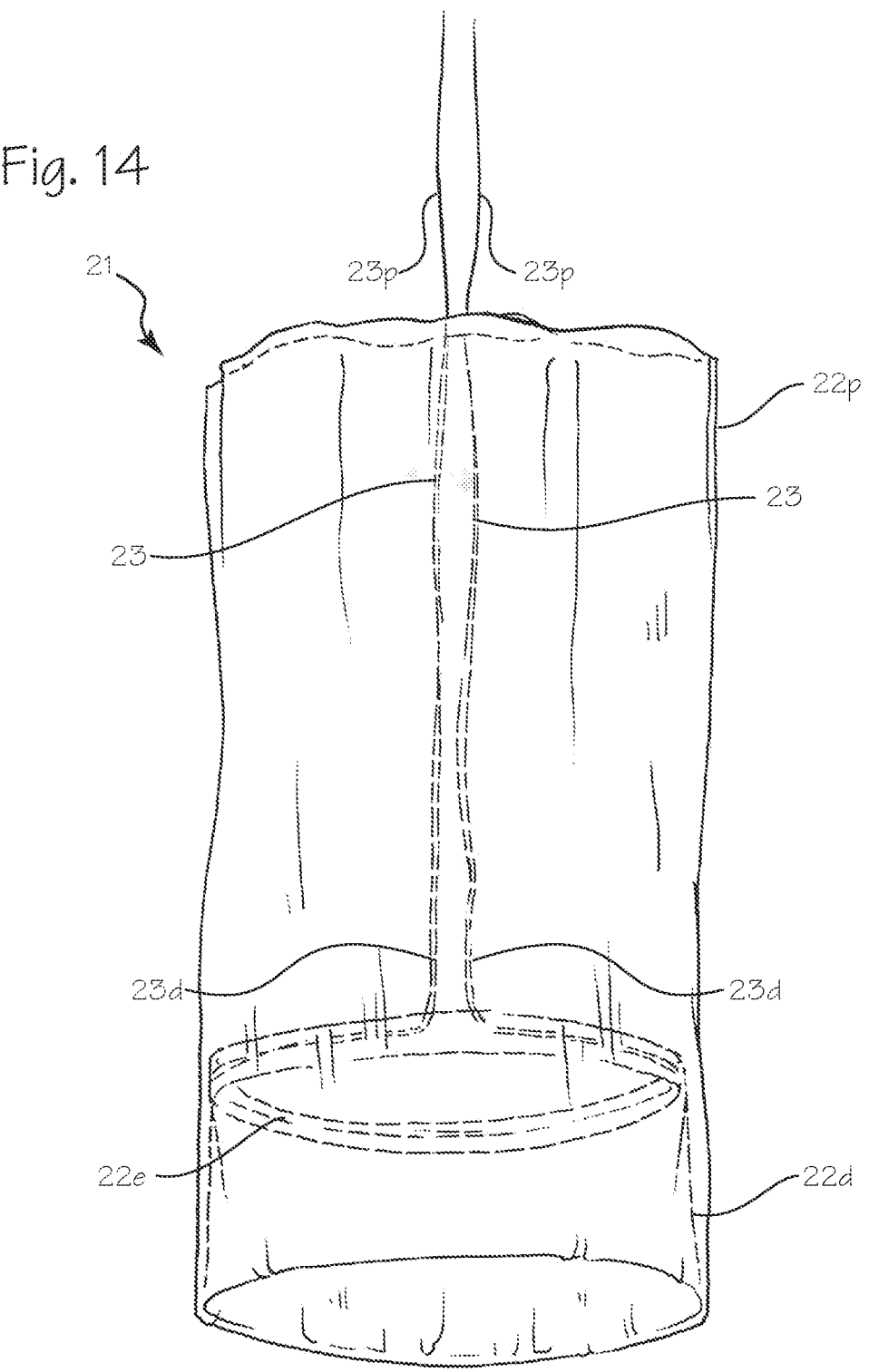
FIG. 14 illustrates the specimen tube assembly of FIG. 12, with a short portion of the distal end of the bag everted within the bag.

FIG. 14 illustrates the specimen tube assembly of FIG. 12, with a short portion of the distal end of the bag everted within the bag. The distal edge is shown folded to the inside of the tube, to form an everted cuff. The process of eversion is used to effectively close off the tube from the workspace, as in the previously described specimen tube assembly, but without the use of the inner channel 3 used FIGS. 1 through 11.

The use of the specimen in conjunction with the rod is illustrated in the following figures.

Figure 15:
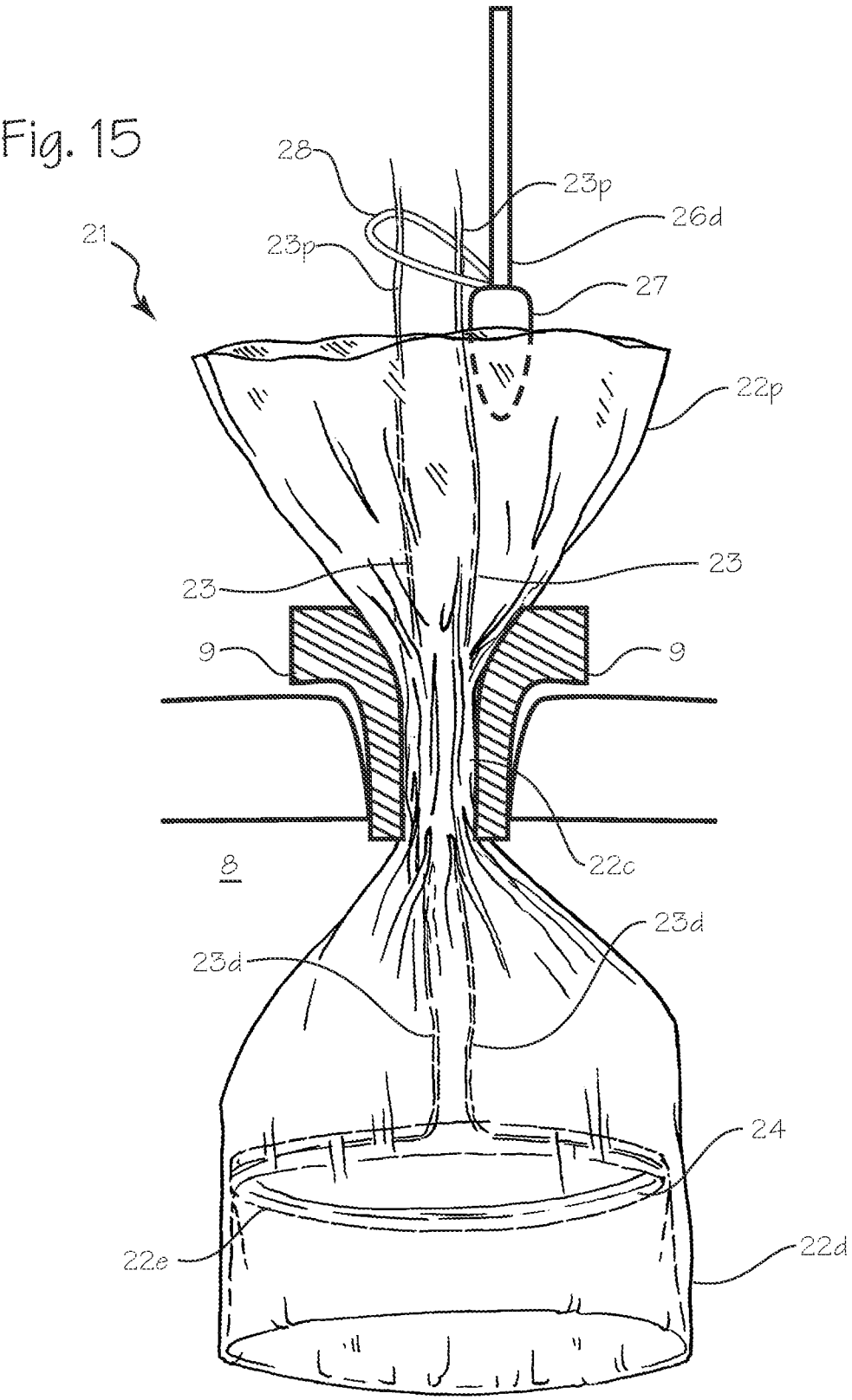
FIG. 15 illustrates the specimen tube assembly of FIG. 12, with the stick of FIG. 13 inserted in the bag and the tether threaded through the guide ring of the stick.

FIG. 15 illustrates the specimen tube assembly of FIG. 12, with the rod 26 of FIG. 13 inserted in the bag and the tether threaded through the semi-rigid guide ring 28 of the rod 26. A user, such a surgeon, will perform each steps to isolate and remove a portion of body tissue that has been dissected from surrounding tissue. As shown in FIG. 15, a surgeon has inserted the specimen tube assembly 22 into the surgical workspace 8 through a cannula or portal 9 which has been placed in an incision in the skin overlying surgical workspace, such that the distal end 22d of the main tube is disposed in the workspace 8, the proximal end 22p of the main tube is disposed outside the body of the patient, with the central portion 22c disposed in the cannula/portal. The hoop 24 in the hem at the distal edge 22e is preferable sufficiently resilient to hold the distal end of the main tube open. The tether proximal end 23p and pull ring 25 (see FIG. 12) remain outside the body. Placement of the specimen tube assembly may be observed with an endoscopic camera, inserted into the surgical workspace through a second portal.

Figure 16:
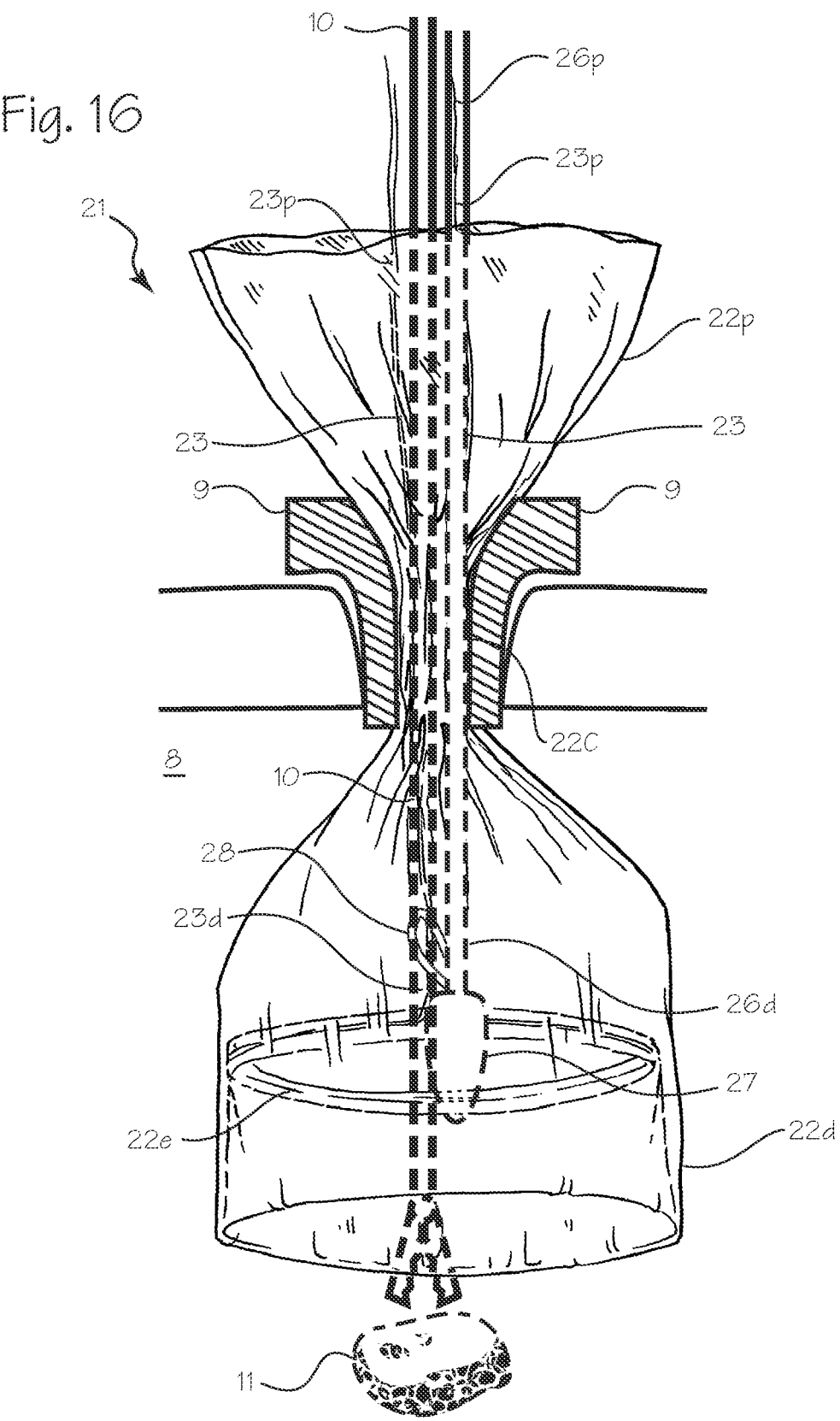
FIG. 16 is a view of the specimen tube assembly of FIG. 12, illustrating insertion of a grasper, through the specimen tube assembly proximal end and into the workspace.
Figure 17:
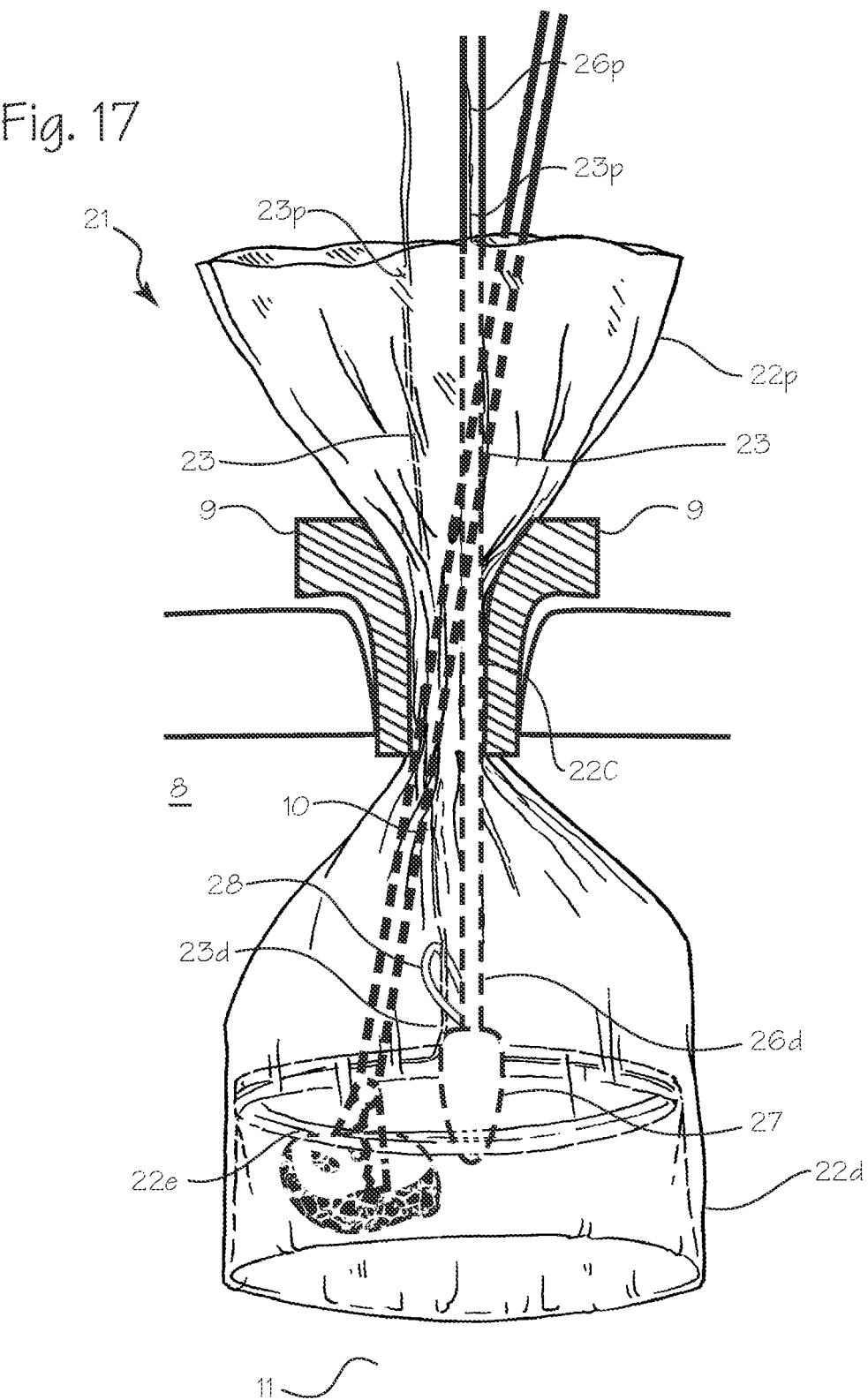
FIG. 17 is a view of the specimen tube assembly of FIG. 12, illustrating drawback of the grasper to place a piece of tissue from the workspace into the specimen tube assembly.

FIG. 16 is a view of the specimen tube assembly of FIG. 12, illustrating insertion of a grasper 10, through the specimen tube assembly proximal end and into the workspace. FIG. 17 is a view of the specimen tube assembly of FIG. 12, illustrating drawback of the grasper to place a piece of tissue from the workspace into the specimen tube assembly. A surgeon, after having placed the bag, inserts the rod 26 and ring 28 into the distal portion of the bag, and also inserts a grasper 10 into the bag, from the proximal end, to position the grasping clamps of the grasper in the workspace. The surgeon then grasps the body tissue and pulls it into the main tube, as shown in FIG. 17. The surgeon may then withdraw the grasper completely from the specimen tube assembly, or may leave the grasper in place, with the tip of the grasper within the distal portion of the bag, to use as a rigid element to facilitate eversion in the next steps.

Figure 18:
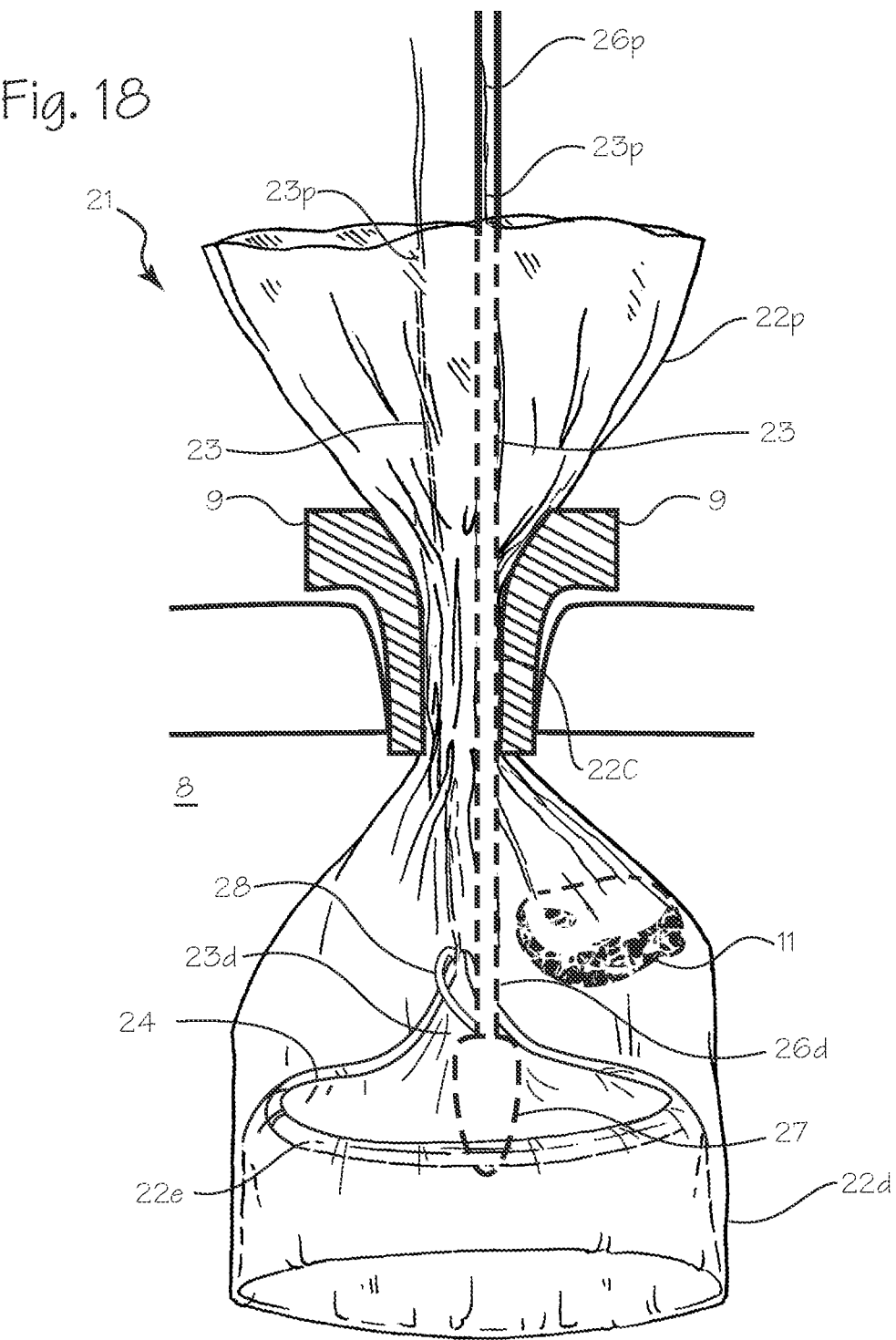
FIG. 18 is a view of the specimen tube assembly of FIG. 12, illustrating initial pullback of the tether, to draw the hoop into the guide ring of the stick.
Figure 19:
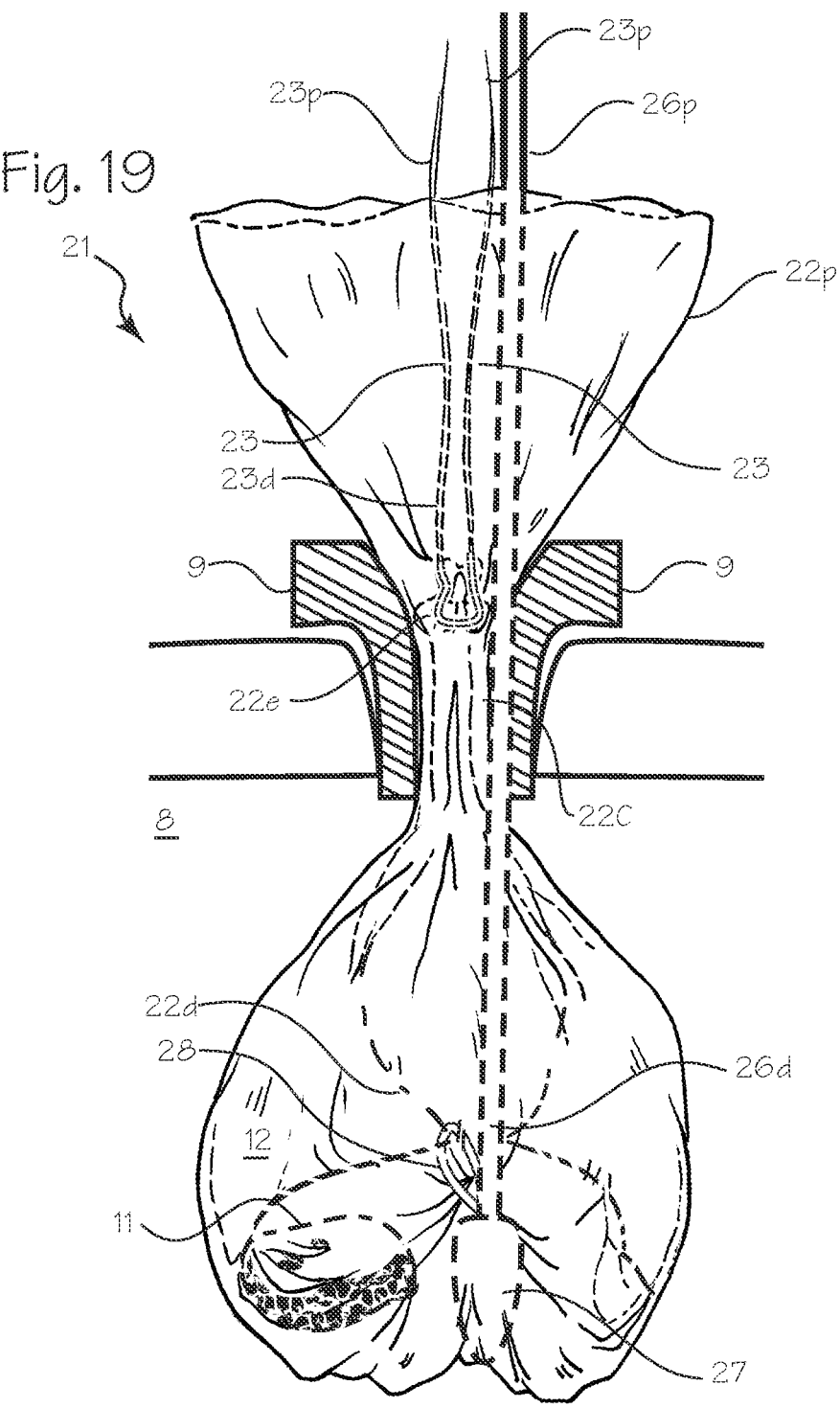
FIG. 19 is a view of the specimen tube assembly of FIG. 12, illustrating a further pullback of the tether to draw the hoop proximally within the guide ring and draw the open distal end of the tube through the guide ring.

FIG. 18 is a view of the specimen tube assembly of FIG. 12, illustrating initial pullback of the tether, to draw the hoop 24 into the semi-rigid guide ring 28 of the stick, while FIG. 19 is a view of the specimen tube assembly of FIG. 12, illustrating a further pullback of the tether to draw the hoop 24 proximally within the guide ring 28 and draw the open distal end of the tube through the guide ring 28. As shown in FIG. 18, the surgeon pulls the tether proximally, using the proximal portions 23p of the tether (and the pull ring 25, if provided), to draw the hoop 24 into the tube 22 and guide ring 28. FIG. 18 shows the hoop 24 just entering the ring 28, while FIG. 19 shows the device with the hoop 24 drawn entirely into the tube, proximal to the guide ring 28, such that the open edge of the main tube is entirely located within the tube itself and the body tissue is isolated from the workspace by the remaining exposed side wall 12 of the main tube. The eversion which occurs in these steps may be facilitated with the blunt end of the rod or the grasper, holding the rod or grasper in place in the main tube distal end to provide a rigid post over which the main tube material can slide while everting through the hoop 24.

Figure 20:
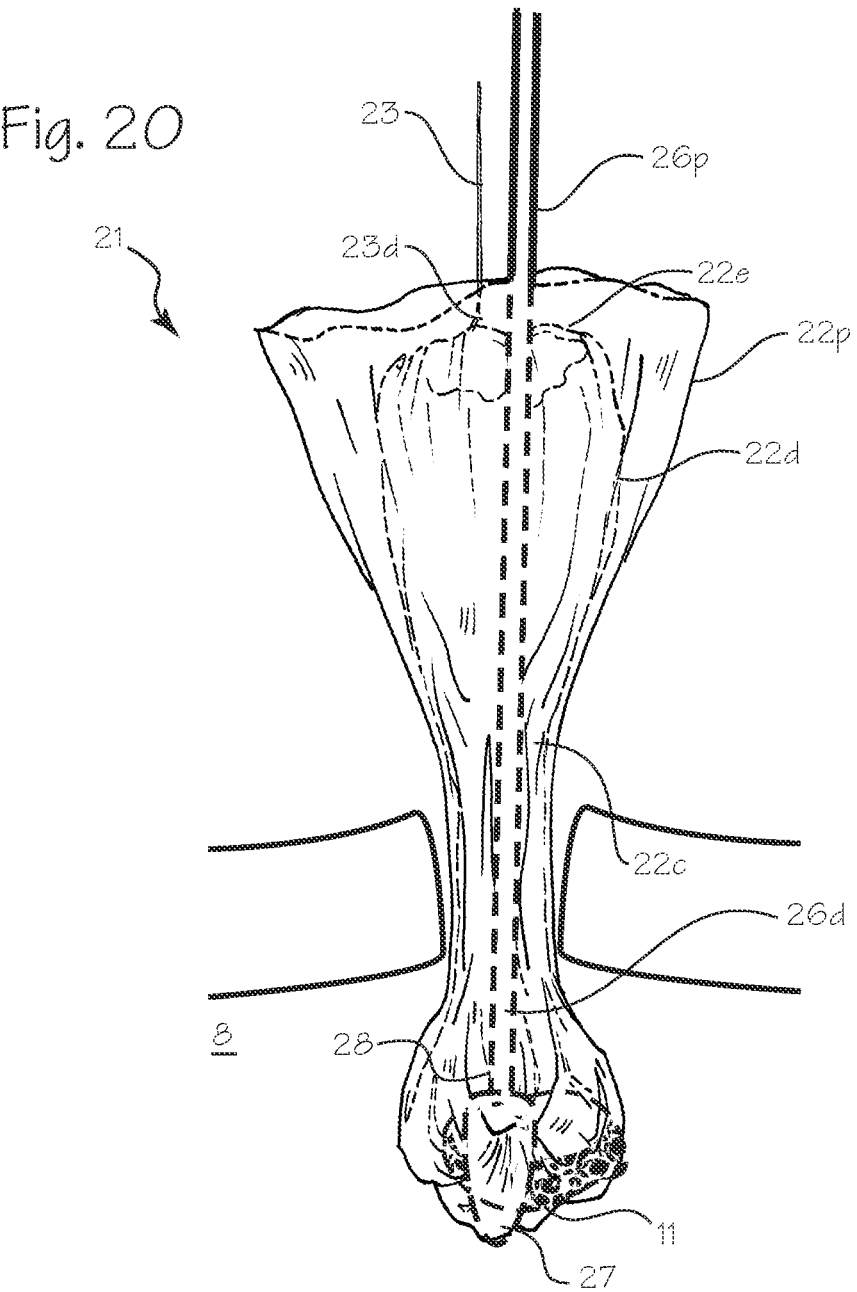
FIG. 20 is a view of the specimen tube assembly of FIG. 12, illustrating a further pullback of the tether to draw the hoop proximally within the tube to reside outside the workspace.

FIG. 20 is a view of the specimen tube assembly of FIG. 12, illustrating a further pullback of the tether to draw the hoop 24 proximally within the guide ring to reside outside the workspace. In FIG. 20, the surgeon has pulled the tether and hoop 24 proximally within the tube, until the hoop 24 and distal edge of the main tube are located entirely outside the body. At this point, any fluids or diseased cells that leak from the distal end of the main tube will spill outside the workspace. Finally, the surgeon will pull the entire specimen tube assembly out of the workspace. The everted distal end of the bag, and the proximal end of the bag, may be tied closed before withdrawal, and the cannula may be withdrawn with the bag or it may be withdrawn before pulling the bag from the workspace.

Figure 21:
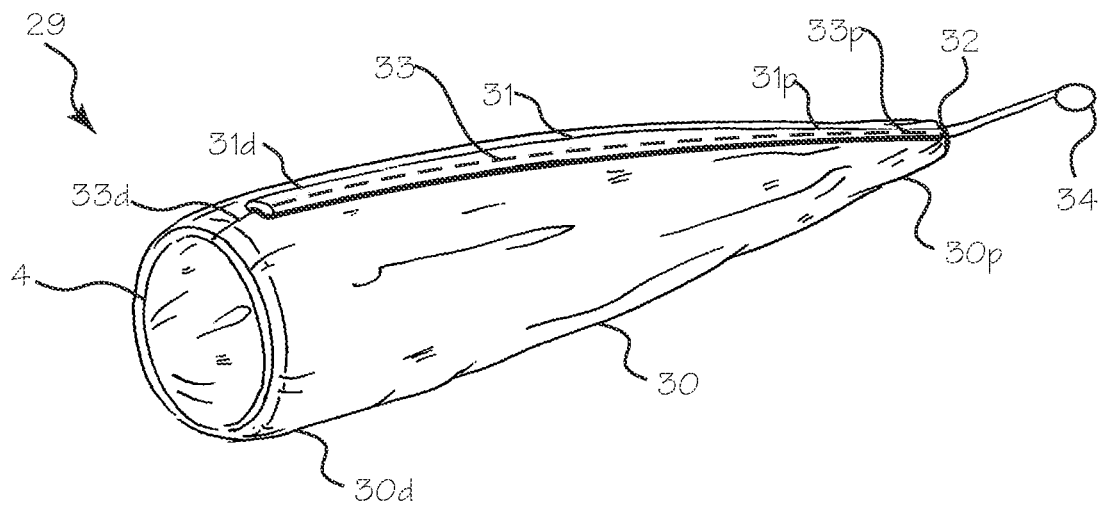
FIGS. 21 through 24 illustrate an embodiment of a specimen tube assembly with rigid or semi-rigid tube in place of the side channel of the device of FIGS. 1 through 11.
Figure 22:
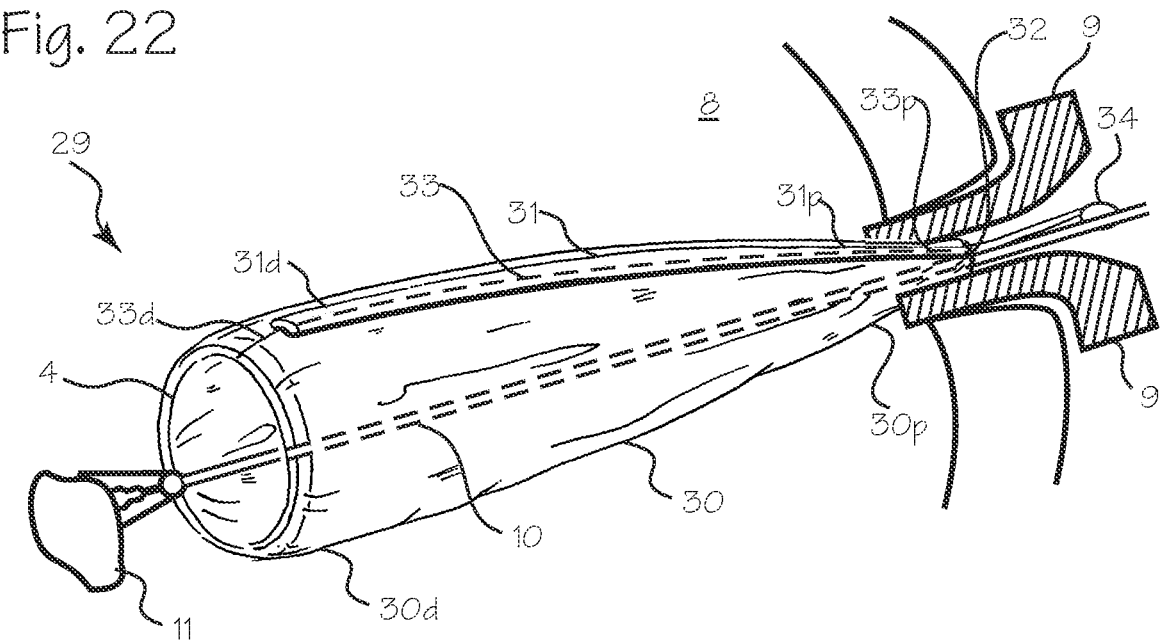
Figure 23:
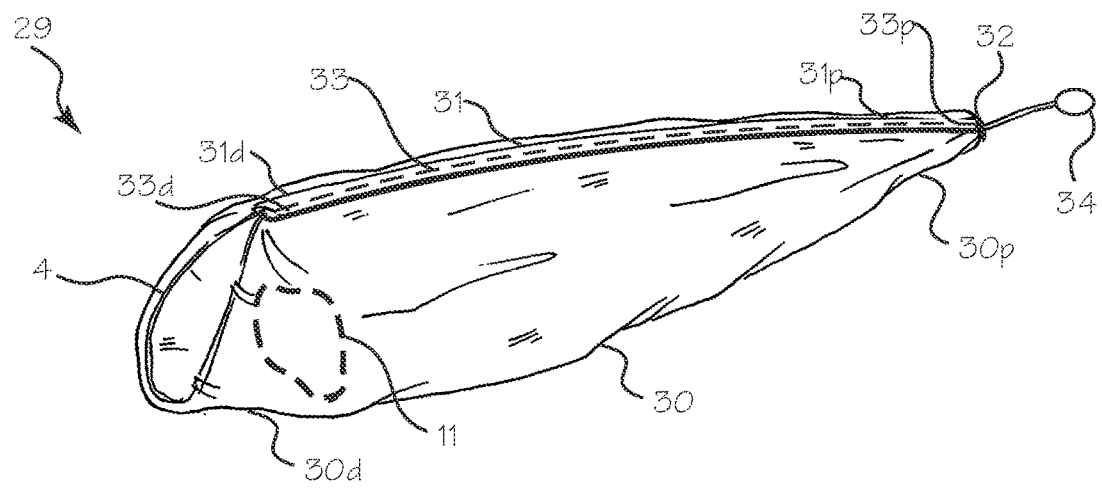
Figure 24:
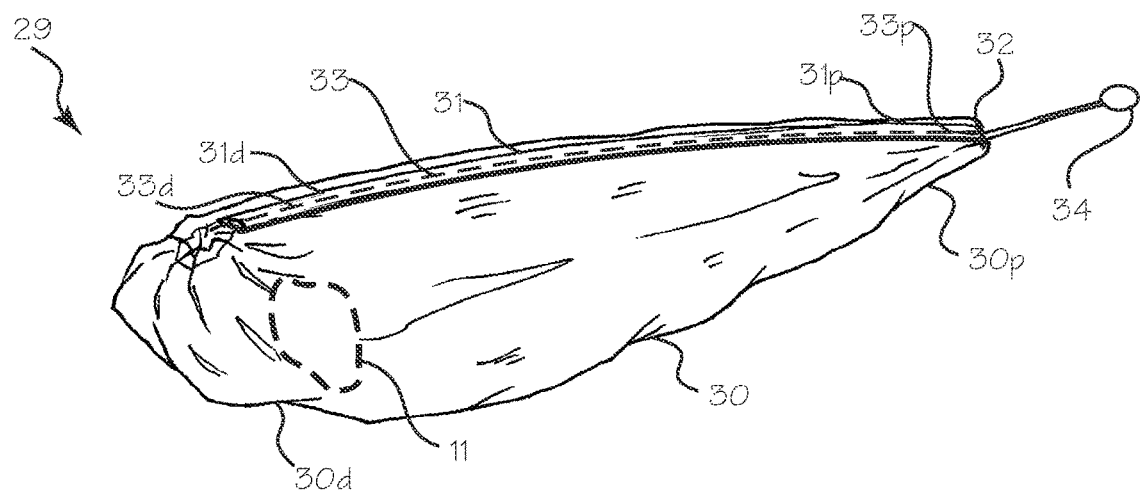

FIGS. 21 through 24 illustrate an embodiment of a specimen tube assembly with rigid or semi-rigid tube in place of the side channel of the device of FIGS. 1 through 11. In FIG. 21, the specimen tube assembly 29, again with main tube 30 with a distal end 30d and a proximal end 30p, and a side channel tube 31, secured within the main tube, with a distal end 31d terminating near the distal end 30d of the main tube 30 (preferably a short distance proximal to the distal end of the main tube), and a proximal end 31p terminating proximate the proximal end 30p of the main tube. An elastic band 32 in the proximal end of the main tube may be provided to hold the proximal edge tight to a grasper. A semi-rigid or resilient hoop 4 may be secured to the distal end of the tube, circumscribing the opening at the distal end. As in FIG. 1, the hoop may be captured in a hem formed by doubling or turning over the edge of the tube on itself and securing it to the tube to create a channel in which the hoop resides, or the hoop may be glued, melted, or integrally formed with the tube. The hoop may be a complete or partial hoop. Preferably, as in the previously described embodiments, the hoop 4 is semi-rigid, with sufficient hoop strength to open the distal end of the tube when unconstrained, and, preferably, a hoop strength greater that the hoop strength of the tube 30. A tether 33 is disposed within the rigid side channel 31, extending from beyond the distal end of the side channel to the proximal end of the side channel and beyond. At the distal end 33d of the tether, the tether is secured to the hoop 4. The proximal end 33p of the tether extends proximally to the proximal end of the side channel and the main tube, and proximally out of the proximal end of both the side channel and the main tube. A pull ring 34 may be attached to the proximal end of the tether. In this device, the side channel tube 31 is rigid or semi-rigid, sufficient to hold the bag suspended. The hoop 4 secured to the distal edge is resilient, and biased to an open configuration. As shown in FIG. 22, the specimen tube assembly has been inserted into a workspace 8, through an incision in the abdominal wall of a patient and a cannula/portal 9 in that incision, with the distal end of tube 30d disposed in the workspace and the proximal end of the tube disposed outside the workspace. The grasper has been inserted, through the tube and cannula, and used to grasp a portion of body tissue to withdraw it into the side channel tube 30. As shown in FIG. 23, the grasper has been withdrawn, and the tether has been pulled proximally to draw the hoop 4 into the rigid side channel tube. Depending on the size of the side channel tube and its rigidity, the hoop 4 may be pulled entirely into the distal end of the side channel tube 30, but no further, or it may be withdrawn further proximally into the side channel tube 30 such that the hoop 4, and the distal edge of the main tube, reside outside the body. With the distal edge disposed within the rigid side channel tube, as shown in FIG. 24, the specimen tube assembly may be pulled from the workspace.

Figure 25:
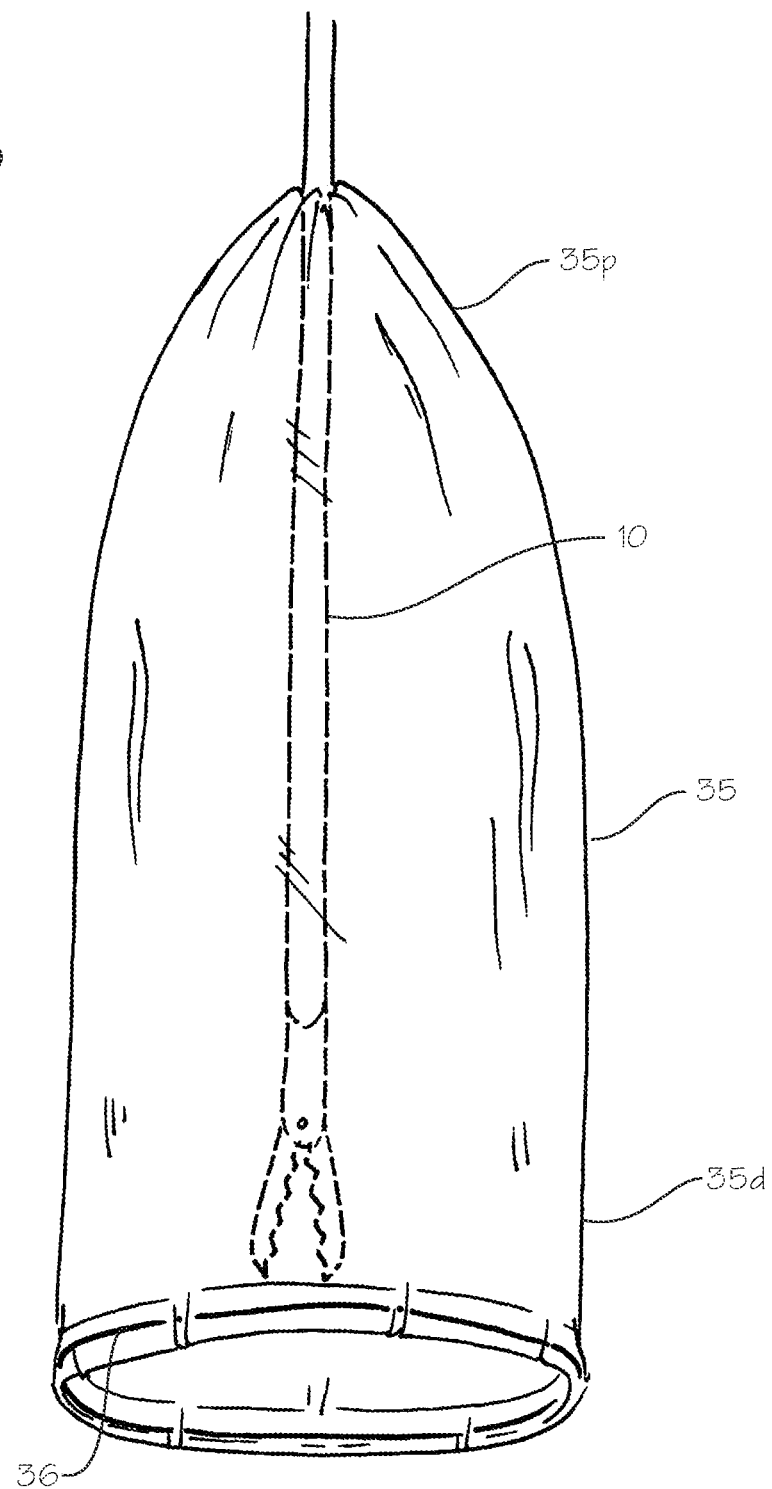
FIGS. 25 through 28 illustrate an embodiment of a specimen tube assembly which is used in conjunction with a grasper and cannula, to draw the distal edge of the bag into the cannula before pulling the bag from the workspace.
Figure 26:
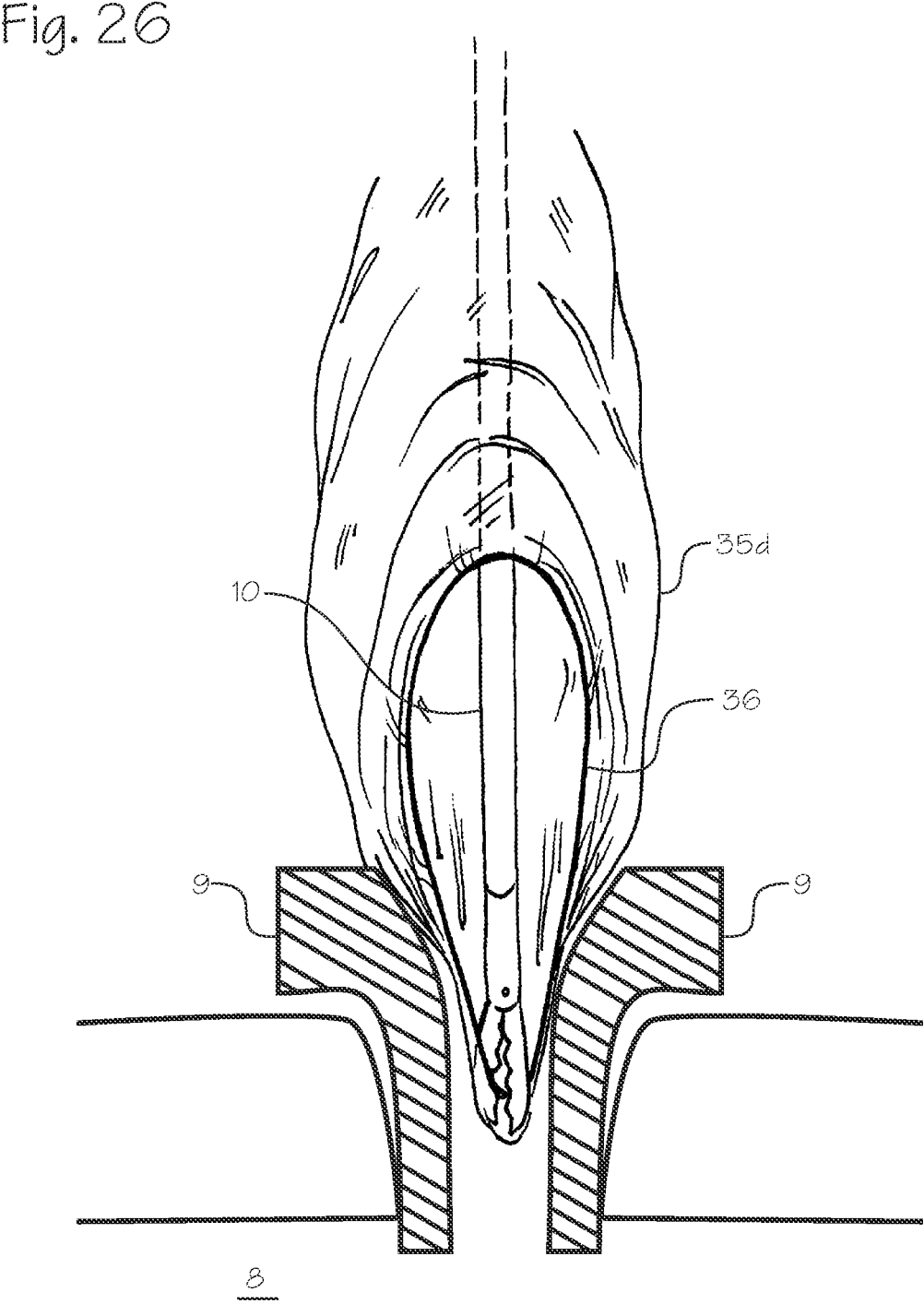
Figure 27:
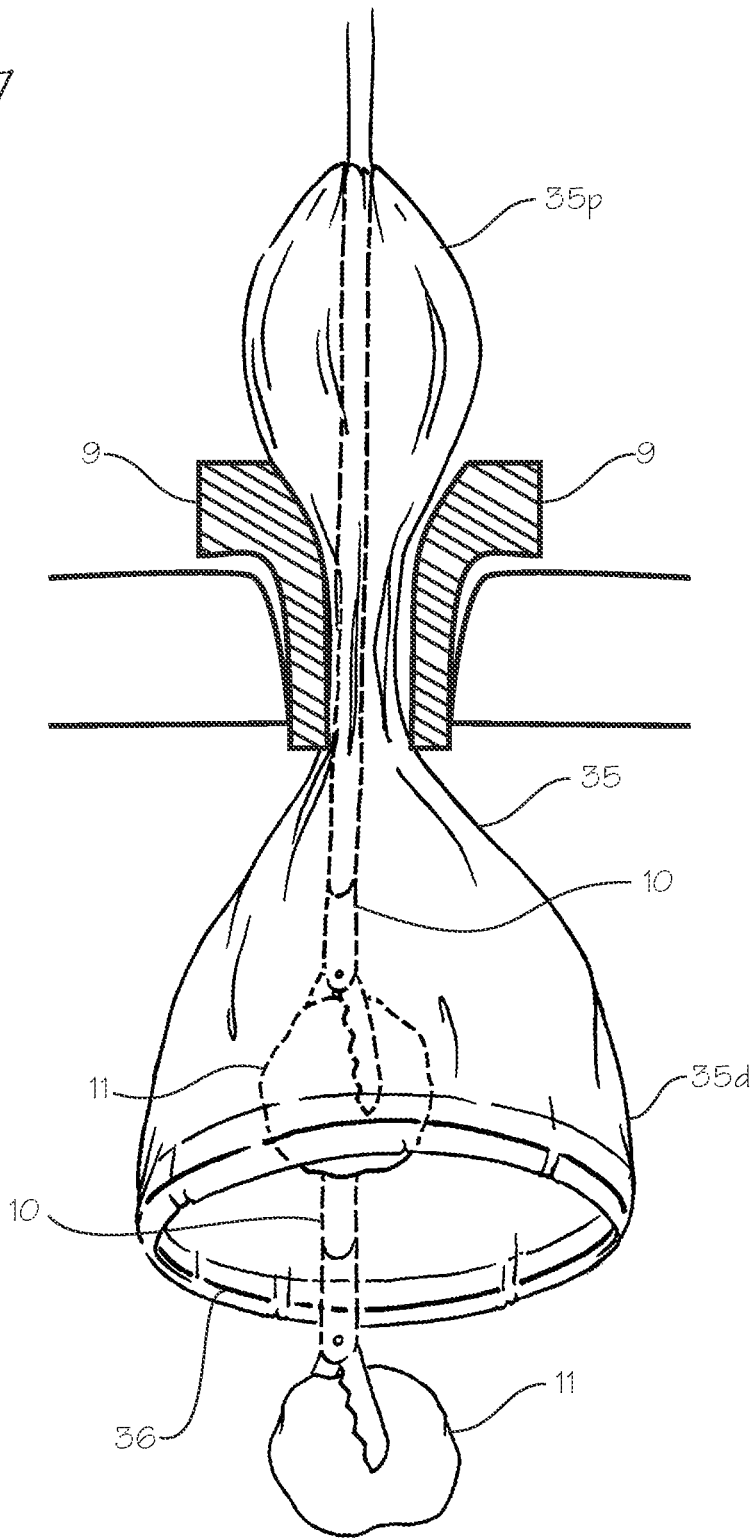
Figure 28:
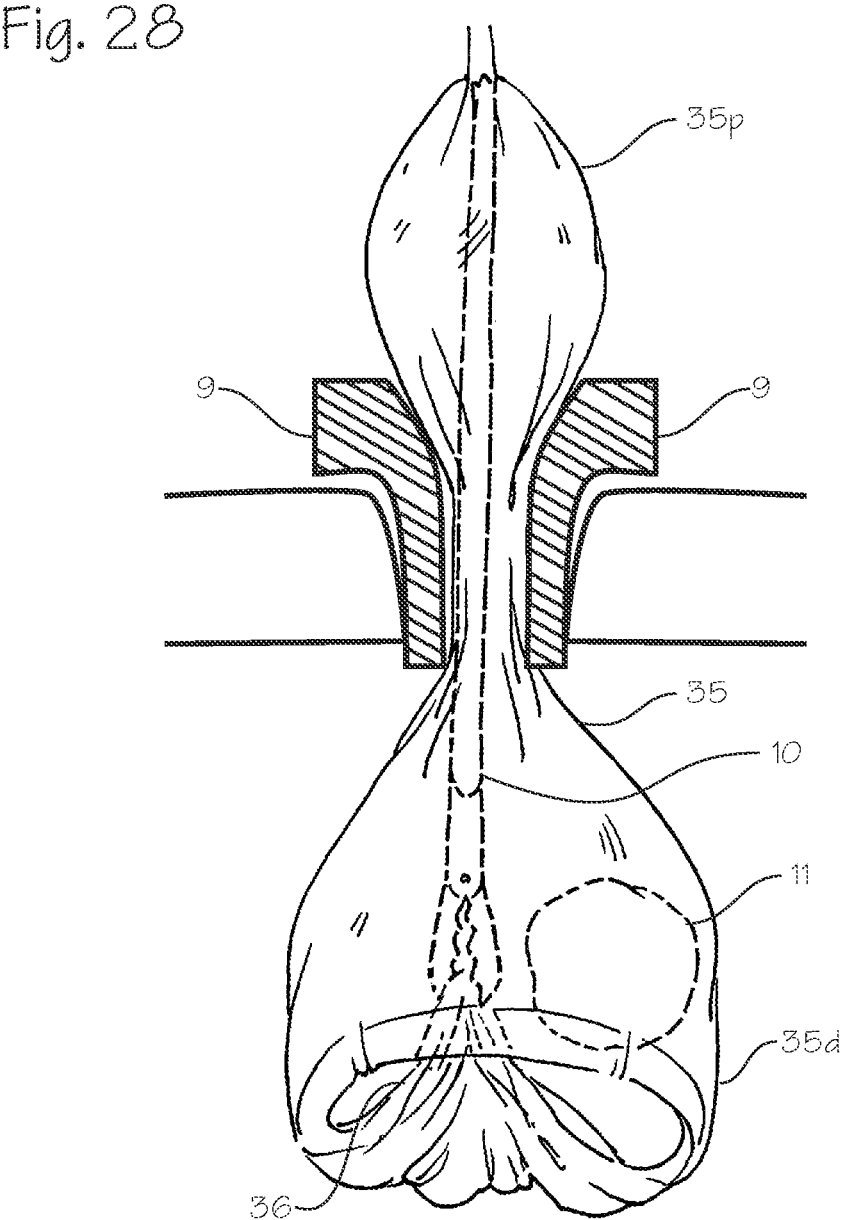

FIG. 25 illustrates a simpler device useful in a method illustrated in the following figures. The device of FIG. 25 includes a tube 35 with an open distal end supported by a hoop 36, and a proximal end secured to the shaft of a grasper 10. The proximal end may be of smaller diameter, to match the outer diameter of the grasper (as in FIGS. 1 through 11), or of large diameter comparable to the distal end (as in FIGS. 12 through 20). Preferably, as in the previously described embodiments, the hoop 36 is semi-rigid, with sufficient hoop strength to open the distal end of the tube when unconstrained, and, preferably, a hoop strength greater that the hoop strength of the tube 35. As shown in FIG. 26, a surgeon inserts the distal end 35d of the tube 35, and the hoop 36, into the workspace, through an opening into the workspace. The surgeon also inserts the grasper through the tube, so that it extends distally into the workspace. This may be done in separate steps (for example, using a cannula to insert the bag, and then inserting the grasper through the bag), or it may be conveniently done by grasping the hoop with the grasper, from inside the tube, and pushing the hoop and tube through the cannula 9 (or inserting the tube through the opening, without using a cannula), and shown in FIG. 26. With the distal end of the tube in place, and the grasper in place within the workspace, the surgeon manipulates the grasper to grasp a portion of body tissue and pull the portion of body tissue into the tube, as shown in FIG. 27. The tube may be held with a second grasper to facilitate placement of body tissue into the tube. With the body tissue within the tube, the surgeon grasps the distal end of tube (for example, by grasping the hoop) with the grasper, as shown in FIG. 28, and pulls the distal end of the tube and/or the hoop through the cannula, leaving a loose portion of the tube in the workspace and pulling the distal end through the cannula and out of the workspace. With the distal end and the proximal end of the tube outside the workspace, the surgeon pulls the entire specimen tube assembly out of the workspace. With this device, the bag need not evert fully before withdrawal, and is sufficient that the distal end of the tube be effectively closed and/or withdrawn from the workspace. Also, the grasper may be inserted side-by-side with the tube, rather than inside the tube, so that upon withdrawal of the grasper and the distal edge of the bag (including the hoop), the bag is folded, rather than turned inside-out, with a central portion of the tube containing the tissue portion.

Figure 29:
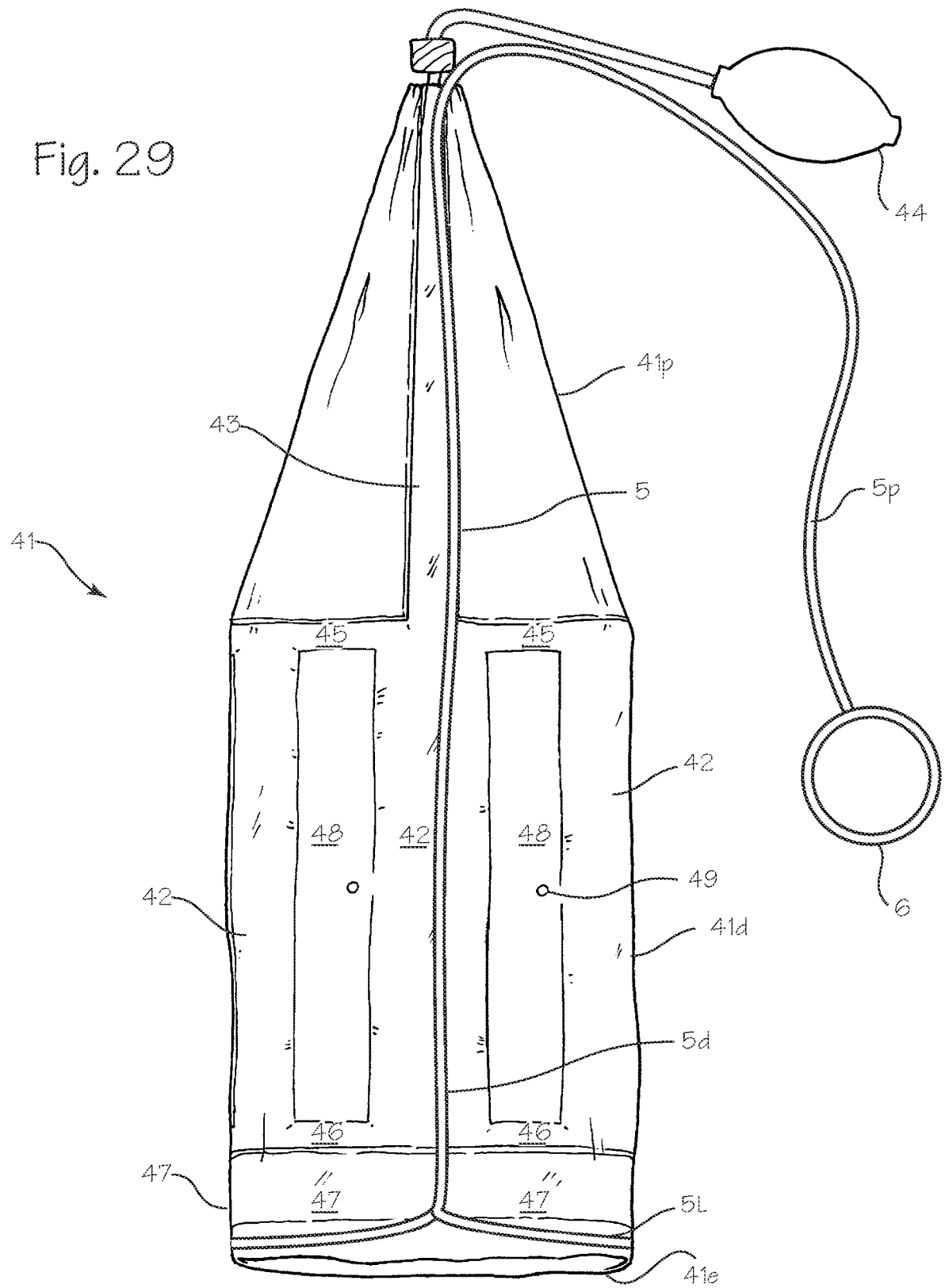
FIGS. 29 and 30 illustrates a specimen tube assembly operable to partially evert to provide an enclosure for specimens obtained in a surgical workspace, held open with inflatable channels.

FIG. 29 illustrates a specimen tube assembly 41 operable to partially evert to provide an enclosure for specimens obtained in a surgical workspace, with inflatable channels which may be inflated to cause the specimen tube assembly to take on a generally cylindrical configuration in the region which, while in use, will reside in the surgical workspace. The overall construction of the specimen tube assembly 41 is similar to the specimen bag assembly of FIG. 1, and includes a main tube 41, with a distal end 41d and a proximal end 41p. The distal end 41d, intended to be inserted into the endoscopic workspace, is substantially isodiametric throughout its length (when inflated). The proximal end 41p, intended to remain in the insertion cannula and extend to the outside the workspace when the device is in use, may be tapered as shown, or may also be isodiametric. A tether or flexible cord 5 circumscribes the distal end of the tube in a loop 5L, and, as with previous figures, the loop may be captured in a hem or casing (a channel with an opening, through which the loop may drawn), which may be formed by doubling or turning over the edge of the tube on itself and securing it to the tube to create a channel in which the tether resides, or the loop may be glued or melted to the tube, or the hoop may be integrally formed with the tube. The tether may completely or partially circumscribe the opening of the tube, secured to the distal edge 41*e*. (A semi-rigid or resilient hoop secured to the distal end of the tube, circumscribing the opening at the distal end (such as hoop 4 of the previous figures), may be used in place of the loop portion of the tether, though absence of hoop strength of the tether, comprised of thread, string or suture, facilitates eversion in this embodiment.) The tether 5 runs distally through the specimen tube assembly, through the main open space of the specimen tube assembly (though it may be is disposed within a side channel, extending from the loop, into the distal end of the side channel to the proximal end of the side channel and beyond). The tether may be discrete or integrally formed with the loop. (The loop and tether may be also formed as a lasso, with an eye of the lasso located where the transition from the loop portion to the running portion is depicted, and the lasso loop corresponding to the loop portion and the lasso spoke corresponding the running portion of the tether.) The tether extends proximally to the proximal end of the specimen tube assembly and proximally out of the proximal end of the specimen tube assembly. A pull ring 6 may be attached to the proximal end 5*p* of the tether. (An additional ring, such as ring 7 shown in the earlier figures, may be disposed at the proximal end or edge of the main tube. This additional ring is preferably rigid or semi-rigid, to hold the proximal end open as needed to accommodate laparoscopic instruments.) As illustrated, the proximal end 41*p* of the specimen tube assembly is funnel-shaped, with a small diameter segment relative to the distal end 41*d* of the specimen tube assembly. However, the specimen tube distal and proximal openings may be roughly the same size, and the tube can be isodiametric throughout its length. Also, the distal end need not be isodiametric, though this construction facilitates eversion.

The specimen tube assembly 41 of FIG. 29 includes several inflatable channels 42, extending longitudinally along the main tube 41. As illustrated, the inflatable channels extend along a distal portion 41*d* of the main tube, and preferable terminate proximally before the proximal end 41*p* (the funnel-shaped portion) of the tube, so that the proximal portion of the main tube is devoid of inflatable channels, so as to minimize the thickness of the proximal portion (the proximal portion of the main tube remains within the cannula when the distal portion is disposed within the endoscopic workspace). An inflation lumen 43 communicates from one or more of the side channels, and runs proximally from the side channel(s) to the proximal end of the main tube, where it can be attached to a pump or syringe 44 operable to inflate the side channels (a ball pump will suffice, but any means for inflating may be used, or the pump may be omitted and the device may be inflated by mouth through a length of tubing). Multiple channels 42 can be fed with inflation fluid through a proximal manifold 45, using a single inflation tube. A distal manifold 46, in fluid communication with the distal ends of the several inflatable channels, may be provided to provide fluid communication between the several inflatable channels at their distal ends. The distal manifold and proximal manifold can facilitate inflation and deflation of the inflatable channels (so that a single inflation lumen may be used). Distal to the distal ends of the channels 42, or the distal manifold 46 (if provided), the main tube may extend distally, without the presence of inflatable channels, in a skirt or edging 47, which is easily everted into the inner volume of the specimen tube assembly. Between each longitudinally extending inflatable channel, a longitudinal extending non-inflatable region 48 of the main tube may be provided. Also, each inflatable channel may be perforated, with a small aperture 49, communicating from the lumen of the channel to the outside channel, either to the outside (as shown) or the inside of the main tube.

Figure 30:
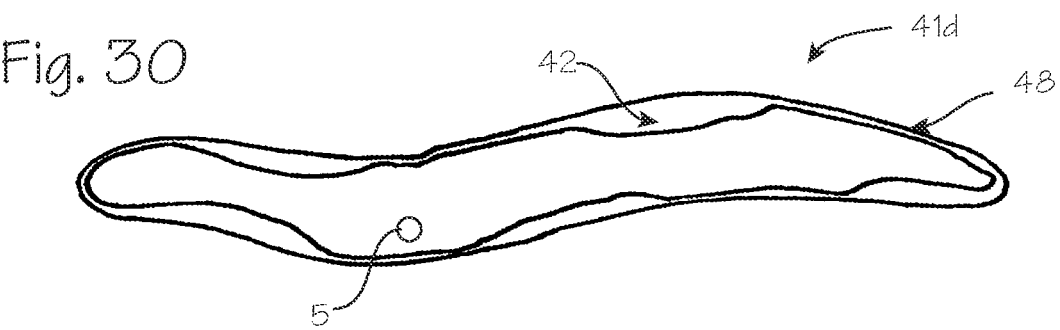
Figure 32:
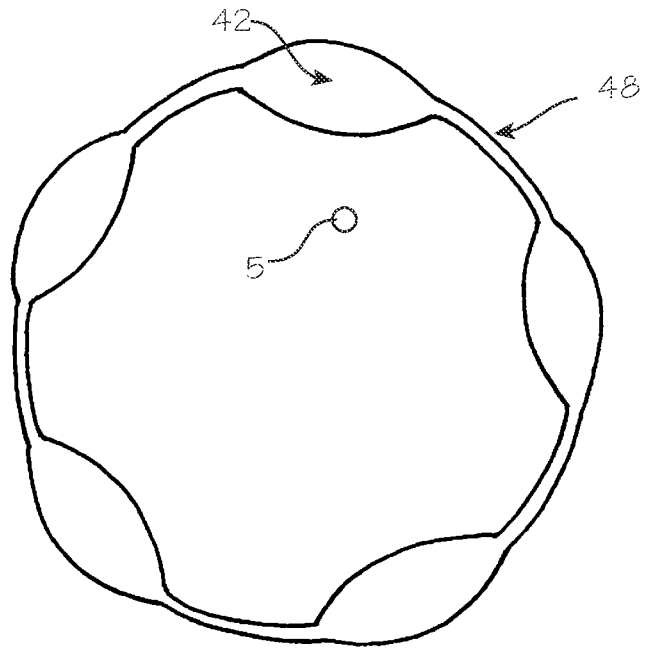
FIGS. 31 and 32 illustrate the configuration of the specimen tube assembly of FIG. 29 when inflated.
Figure 31:
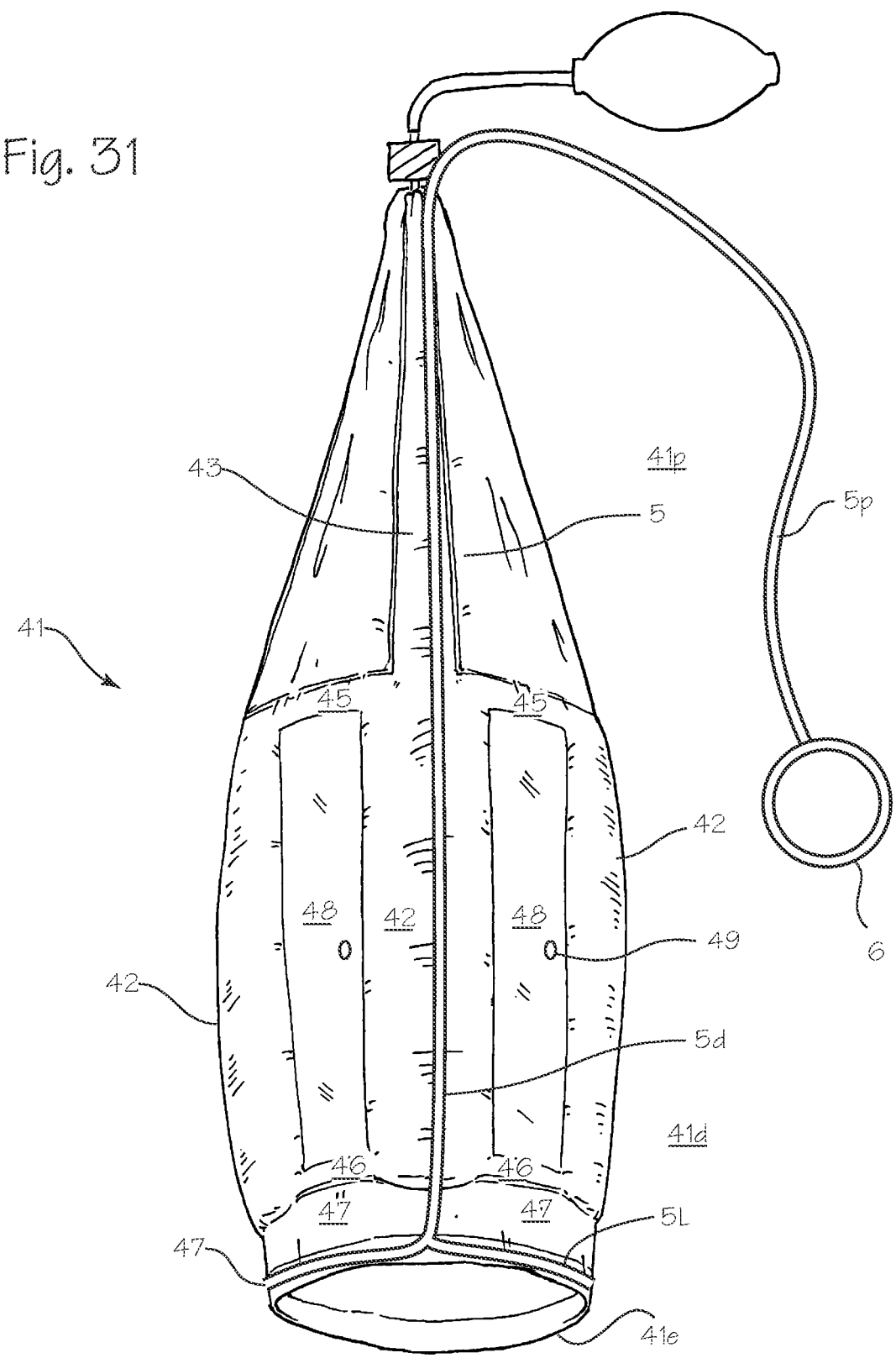

FIG. 31 illustrates the configuration of the specimen tube assembly of FIG. 29 when inflated. Each inflatable channel is bulging due to the pressure of fluid pumped into the channel. Where apertures 49 are provided in the channels, the channels will inflate, and remain inflated, so long as the fluid is provided at a high rate, compared to the leakage through the apertures. As shown, the inflatable channels, when inflated, provide sufficient rigidity/hoop strength or bending stiffness to the specimen tube assembly to hold the very distal end open. FIG. 30 shows, in cross section, the configuration of the specimen tube assembly in the region of the inflatable channels when the inflatable channels 42 are not inflated, so that the tube may be compacted with an insertion cannula, while FIG. 32 shows the configuration of the specimen tube assembly when the inflatable channels are inflated and the specimen tube assembly is expanded. In the inflated configuration, the inflatable channels 42 are distended, as shown in FIG. 32, and hold the main tube in a roughly open cylindrical configuration. The tube, in the region of the inflatable channels, need only be open enough to hold the distal fringe open enough to allow introduction of a tissue specimen, from the workspace, with minimal or no manipulation of the distal opening of the specimen tube assembly from outside the specimen tube assembly, or with an endoscopic tool inserted through a separate portal (other than the possible circumstance in which pulling the specimen into the specimen tube assembly catches the fringe and deflects it toward an everted configuration).

The materials and dimensions of the specimen tube assembly of FIGS. 29 and 31 may vary according to the size of the expected specimen to be collected and the size of the workspace. For retrieval of a gall bladder from the abdomen of a patient, the specimen tube assembly may be provided in configuration with five inflatable channels dispersed about the circumference of the specimen tube assembly, with a flat, non-inflatable region between each inflatable channel. For other applications, a single narrow channel spanning a small circumferential arc of the specimen tube assembly may be used, and in other applications several or many channels 42 may be provided, with or without intervening flats 48.

The specimen tube assembly may be made of various materials, and a suitable fabrication comprises two layers, or two tubes, each comprising a nylon film, a polyurethane film, or a fabric. The specimen tube assembly of FIGS. 29 and 31 can be fabricated with two tubes of nylon film, one disposed within the other, and heated sealed or melted together in the areas corresponding to the flats 48, the skirt 47, and the non-inflatable regions proximal to the proximal manifold or the proximal ends of the inflatable channels. Alternatively, each inflatable channel, manifold and inflation lumen may be formed individually, by adhering a strip of material, or an entire discrete tube, to the inner or outer surface of the main tube. The base layer of the tube, for example a nylon fabric, may be coated with a first layer of urethane, and a second layer of silicone.

Suitable dimensions for the specimen tube assembly, for use in gall bladder retrieval are about six inches (15 cm) long and five inches (13 cm) wide (when laid flat, which provides about 3.2 inch (8 cm) lumen when expanded), with five inflatable channels about 1" (2.5 cm) wide dispersed about the circumference of the specimen tube assembly, with flats of about 1 inch (2.5 cm) wide between each inflatable channels. The skirt may extend 1 or 2 inches (2.5 to 5 cm) distally from the distal end of the inflatable channels. This size, when fabricated with nylon film with a wall thickness of about 6 mil (for a combined wall thickness of 12 mil), will fit through a 12 mm (ID) trocar typically used for endoscopes and staplers, and may be used to retrieve a specimen of about 1.5" by 4" (a typical gall bladder). The dimensions may be adjusted to make the specimen tube assembly suitable for other applications, such as removal of portions of the stomach.

Figure 33:
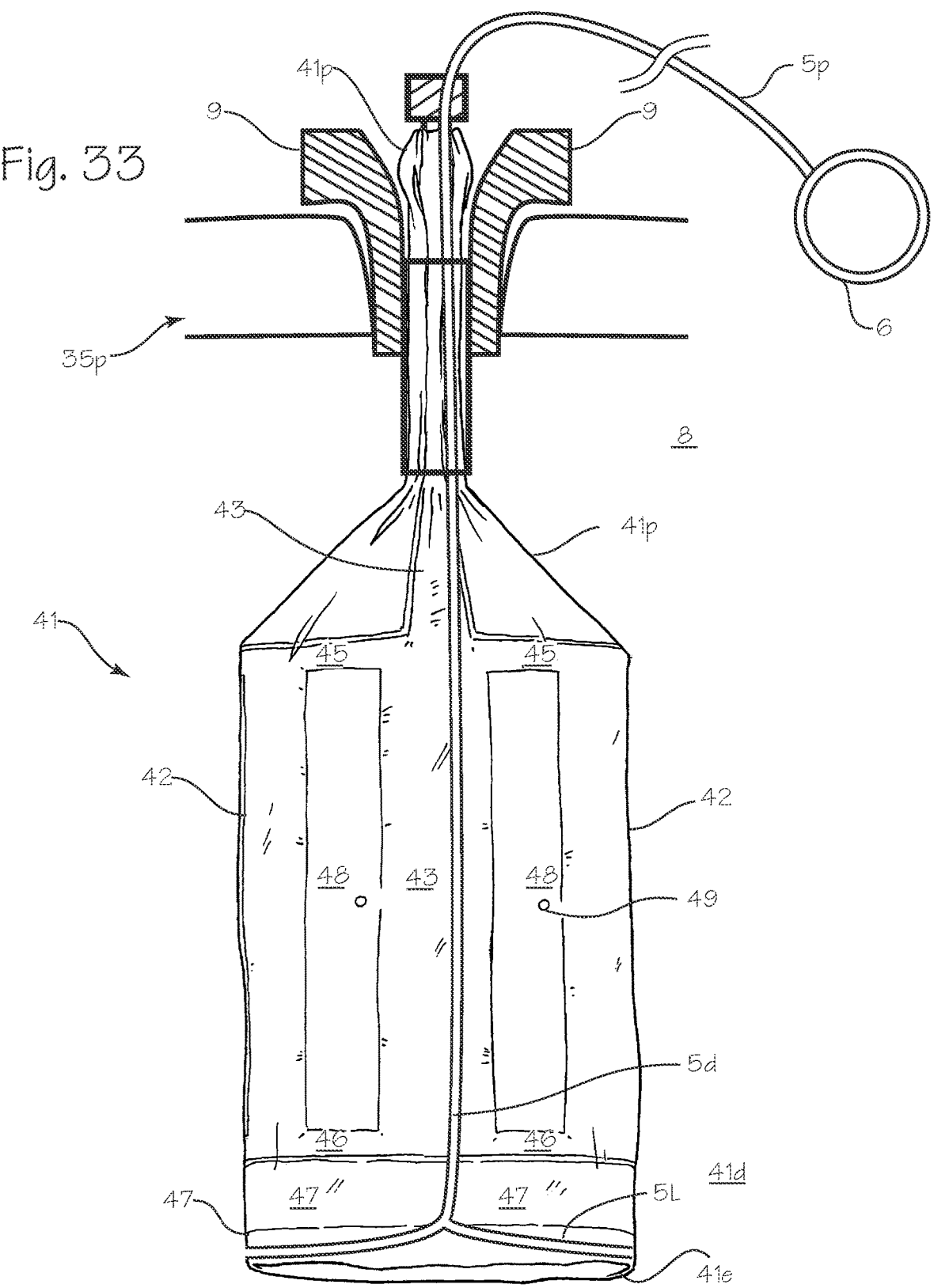
FIG. 33 is a view of the specimen tube assembly of FIGS. 29 and 31, illustrating placement of the device in a surgical workspace.

FIGS. 33 through 38 illustrate the use of the specimen tube assembly of FIGS. 29 and 31. A user, such as a surgeon, will perform each step to isolate and remove a portion of body tissue that has been dissected from surrounding tissue. For insertion through a cannula, the specimen tube assembly 41 is tightly wrapped around an obturator and passed through the cannula. As shown in FIG. 33, a surgeon has inserted the specimen tube assembly 41 into the surgical workspace 8 through a cannula or portal 9 which has been placed in an incision in the skin overlying the surgical workspace, such that the distal end 41d and distal portion of the specimen tube assembly 41 is disposed in the workspace 8, the very proximal end 41p of the specimen tube assembly is disposed outside the body of the patient, with a portion of the proximal end 41p is disposed in the cannula/portal. The loop 5L of tether 5, if comprised of suture, is insufficiently resilient to hold the distal end of the specimen tube assembly open, so the specimen tube assembly will typically be collapsed and floppy in its un-inflated configuration. The tether proximal end 5p and pull ring 6 remain outside the body. Placement of the distal end of the specimen tube assembly may be observed with an endoscopic camera, inserted into the surgical workspace through a second portal, or through the same cannula 9 used for the specimen tube assembly.

Figure 34:
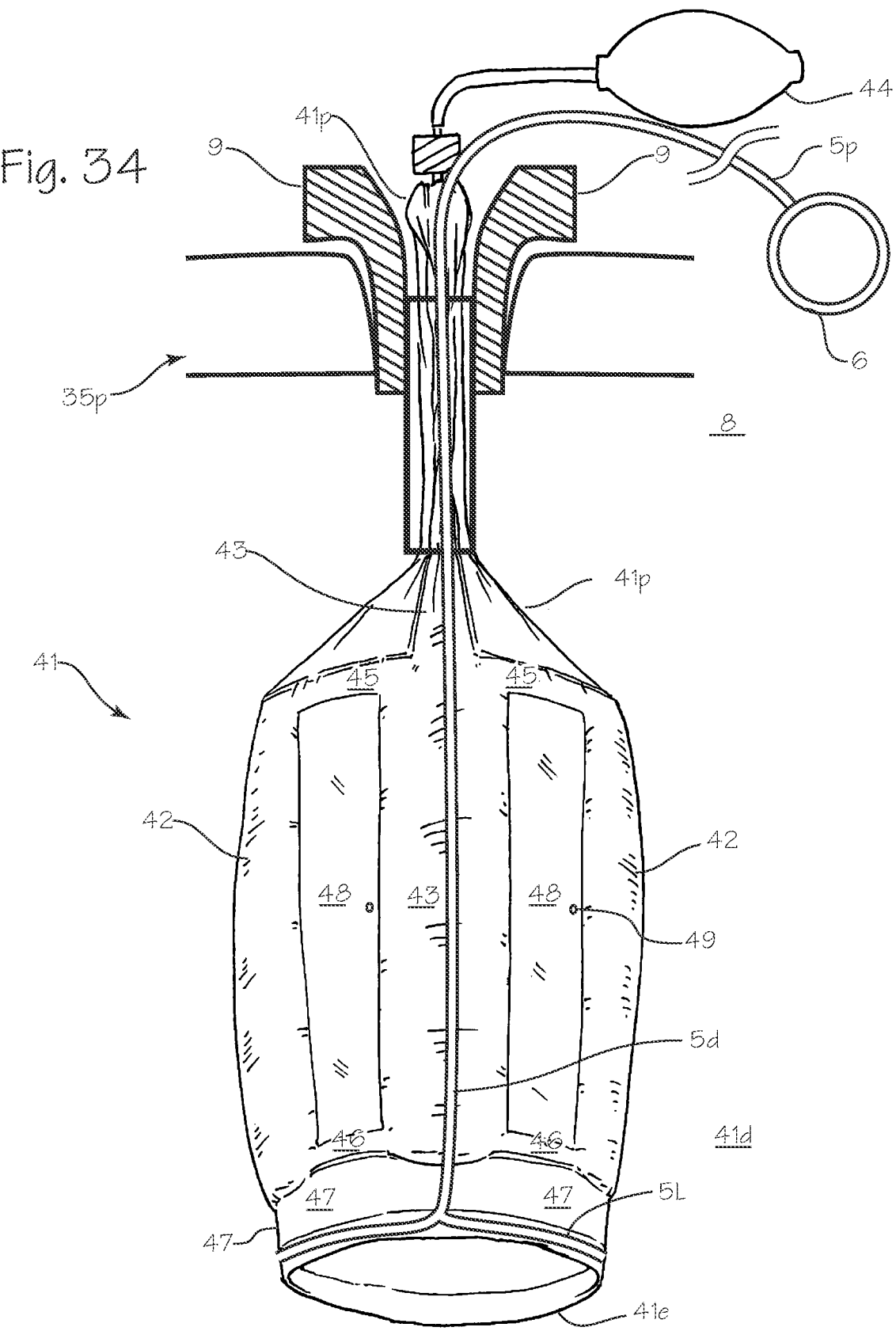
FIG. 34 is a view of the specimen tube assembly of FIGS. 29 and 31, illustrating inflation of the inflatable channels and expansion of the device within a surgical workspace.

As shown in FIG. 34, after insertion of the specimen tube assembly and placement of the distal portion in the workspace, the surgeon operates the pump or syringe 44 to inflate the inflatable channels 42. Upon inflation of the channels, the specimen tube assembly takes on an open configuration as shown in FIG. 31, in the skirt 47 and distal edge 41e are held open sufficiently to allow passage of a grasper jaws in the opening, allow passage of a tissue specimen into the now open central lumen of the specimen tube assembly.

Figure 35:
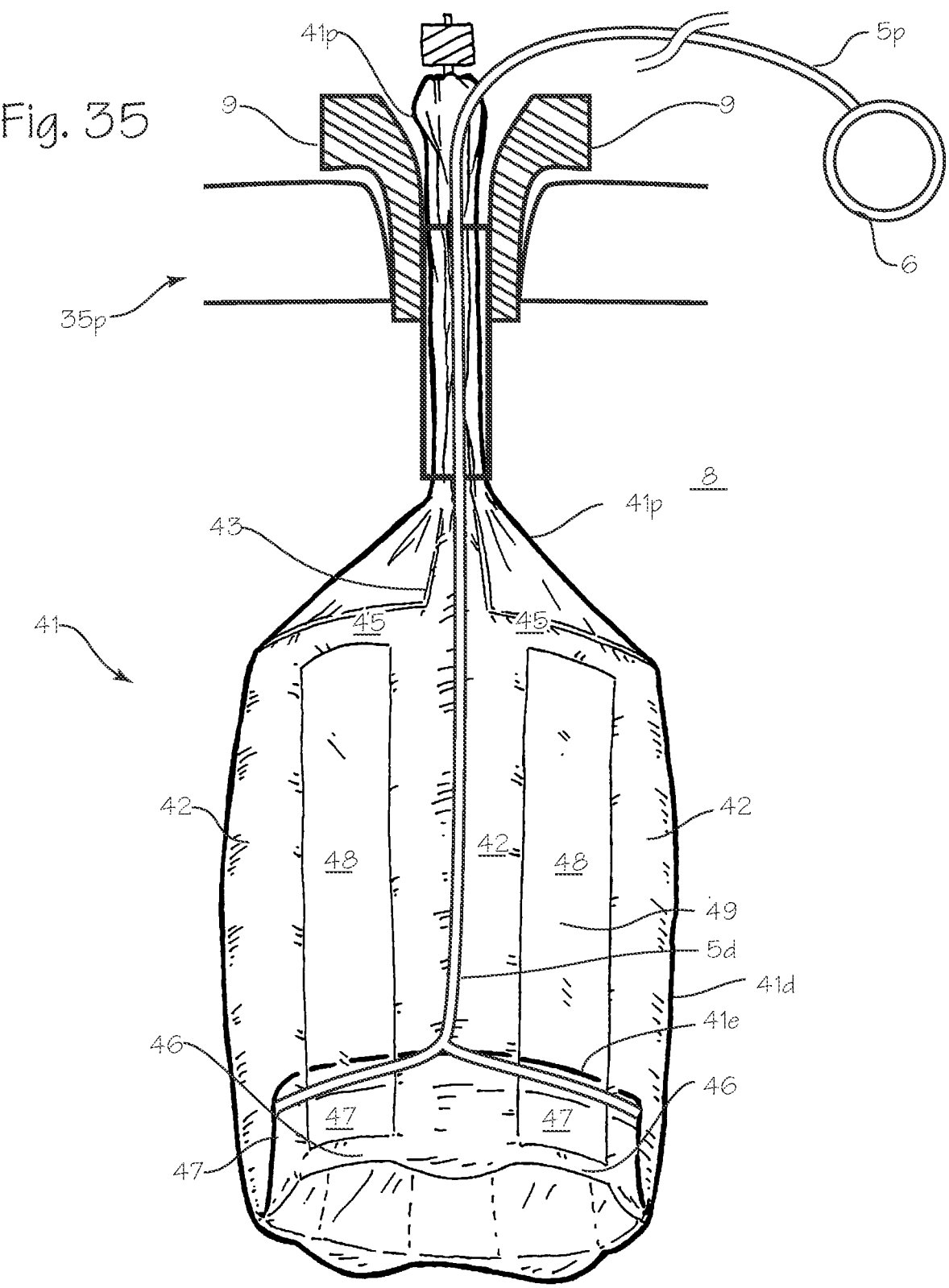
FIG. 35 is a view of the specimen tube assembly of FIGS. 29 and 31, illustrating initial eversion of the skirt into the lumen of the of device.

As shown in FIG. 35, the surgeon has pulled the skirt 47 into the lumen of the specimen tube assembly, by pulling proximally on the proximal end 5p of the tether. (Initial eversion of the skirt may also be caused when the surgeon pulls the tissue into the lumen, if the tissue catches the skirt). In this configuration, the skirt is everted into the main lumen of the specimen tube, such that inner surface of the tube in the region of the skirt now opposes the inner surface of the tube in the more proximal region of the tube distal portion 41d. This step may be performed before or after the steps of pulling a specimen into the tube.

Figure 36:
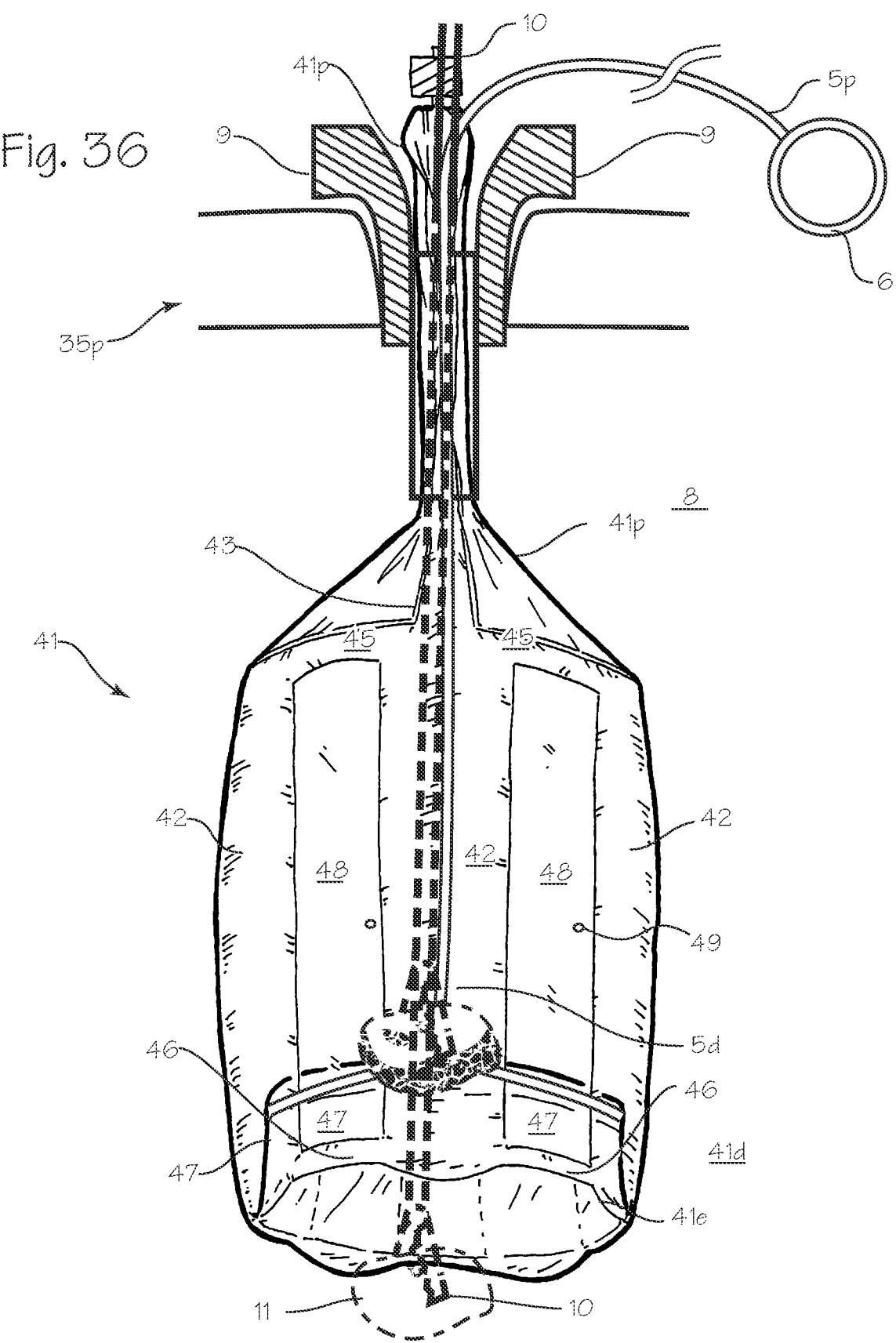
FIG. 36 is a view of the specimen tube assembly of FIGS. 29 and 31, illustrating initial deposit of the specimen into the lumen of the device.

As shown in FIG. 36, the surgeon inserts a grasper 10 into the specimen tube assembly, from the proximal end, to position the grasping jaws of the grasper in the workspace. The surgeon then grasps the body tissue, item 11, and pulls it into the specimen tube, and releases the tissue within the lumen of the specimen tube assembly. The grasper is preferably freely movable within the tube, but it may be secured to the proximal end of the tube by the additional ring 7 (shown in the previous figures), using an elastic ring, or by fixing the ring to the grasper with adhesive.

Figure 37:
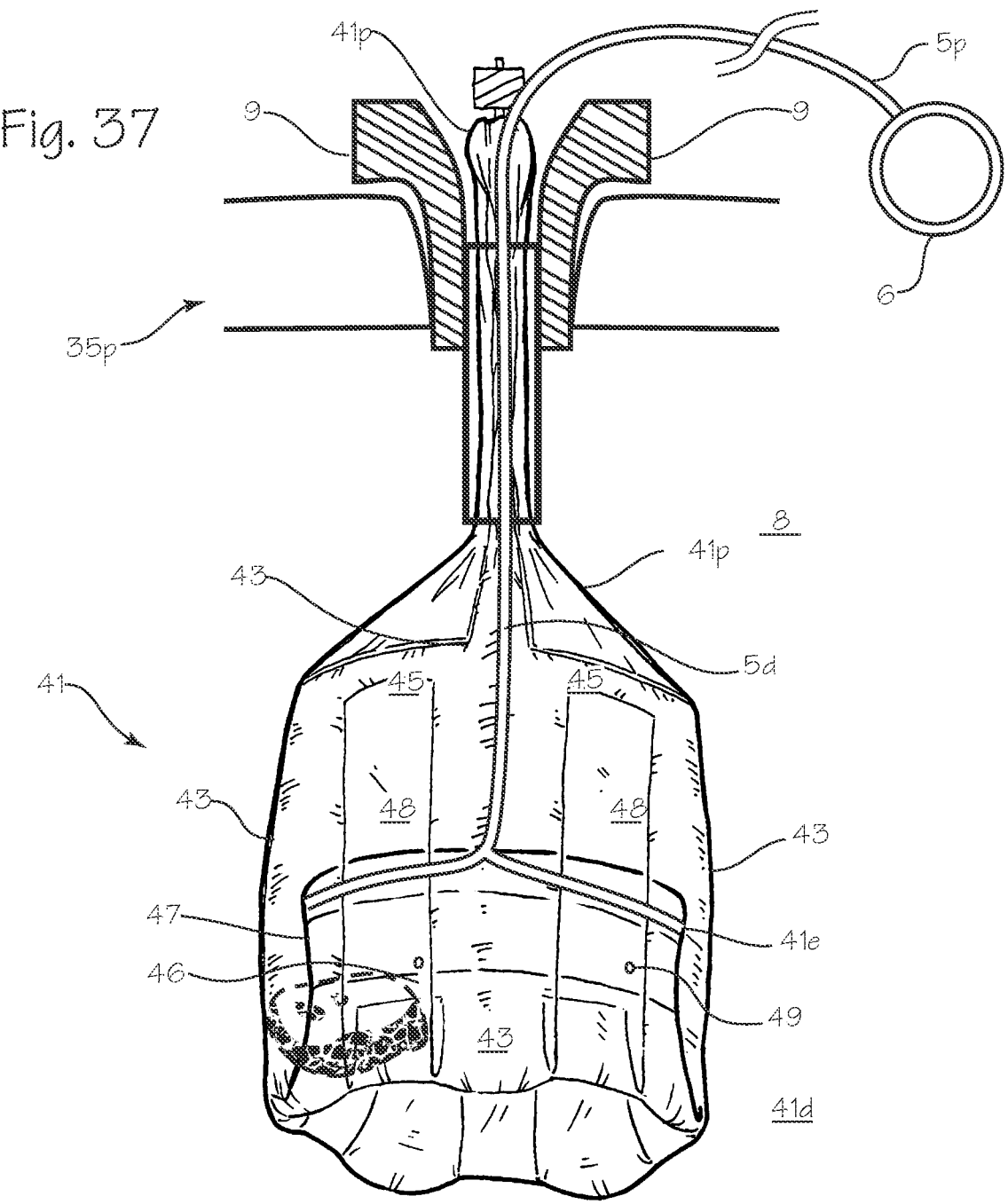
FIG. 37 is a view of the specimen tube assembly of FIGS. 29 and 31, illustrating eversion of the skirt and distal portions of the inflatable channels into the lumen of the device.

As shown in FIGS. 36 and 37, the surgeon pulls the tether proximally, using the proximal portions 5p of the tether (and the pull ring 6, if provided), to draw the skirt into the open lumen of the specimen tube assembly. FIG. 36 shows the skirt just entering the lumen of the specimen tube assembly, while FIG. 37 shows the device with the skirt drawn entirely into the lumen, and the distal portions of the inflatable channels everted into the lumen, create an everted portion of the tube within an un-everted portion of the tube. As depicted in FIG. 37, the tissue 11 is trapped between the inner wall of the everted distal portion of the specimen tube assembly and the inner wall of the more proximal un-everted portion of the distal portion of the specimen tube assembly. With the specimen securely trapped, the specimen tube assembly need not be maintained in the expanded configuration. The surgeon at this point, when the specimen is sufficient secure, opens the inflation lumen (opening a bleed valve or just disconnecting the ball pump), and begins bleeding fluid from the inflatable channels (the process of deflation can be started at any time in the overall procedure after the specimen is pulled into the specimen tube assembly). The surgeon may continue pulling proximally on the tether, to compress the inflatable channels and force fluid more quickly from the inflatable channels. The apertures 49, if provided, will facilitate deflation by allowing fluid to escape through an additional route, especially if the channels are collapsed so as to close off flow to the proximal manifold and inflation lumen. The surgeon may also operate an associated pump to evacuate the inflatable channels. When the specimen tube assembly is sufficiently deflated, and the tube sufficiently everted to avoid or minimize leakage of any fluid or tissue associated with the retrieved tissue, the surgeon pulls the specimen tube assembly from the body, taking advantage of the elasticity of the skin to pull even large specimens through the small skin incision. The cannula/portal may be removed prior to removal of the specimen tube assembly, or with the specimen tube assembly.

Figure 38:
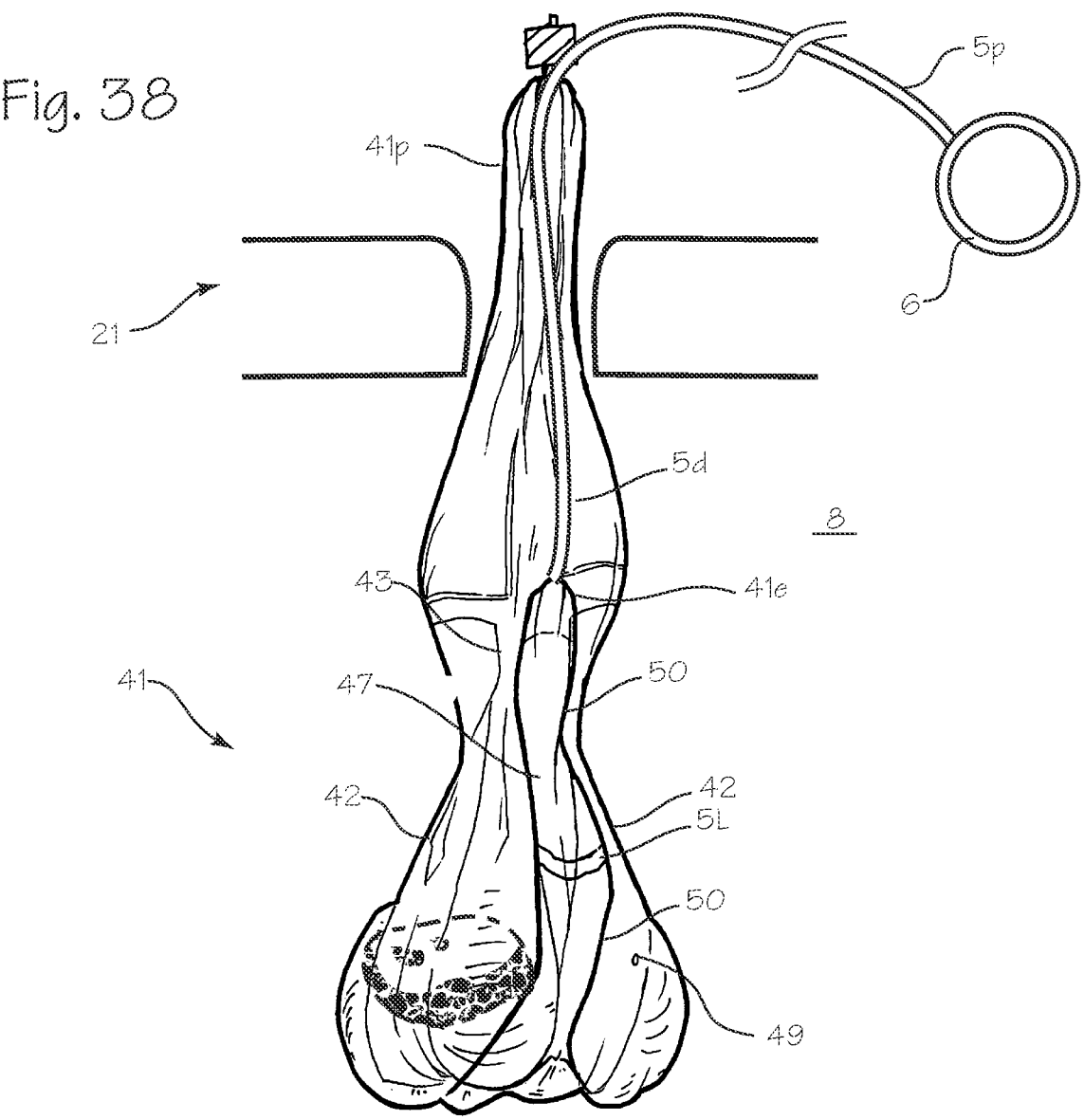
FIG. 38 illustrates withdrawal of the specimen tube assembly of FIGS. 29 and 31 from the workspace.

FIG. 38 illustrates withdrawal of the specimen tube assembly from the workspace of FIGS. 29 and 31. With the specimen securely trapped between the everted distal portion of the specimen tube assembly and the un-everted remainder of the specimen tube assembly, with the now-folded portion 50 isolating the specimen from the workspace, the surgeon can continue to collapse the specimen tube assembly, and pull the collapsed or semi-collapsed specimen tube assembly through the incision, forcing the incision and surrounding skin to stretch as necessary to allow passage of the specimen tube assembly and specimen from the workspace.

Figure 39:
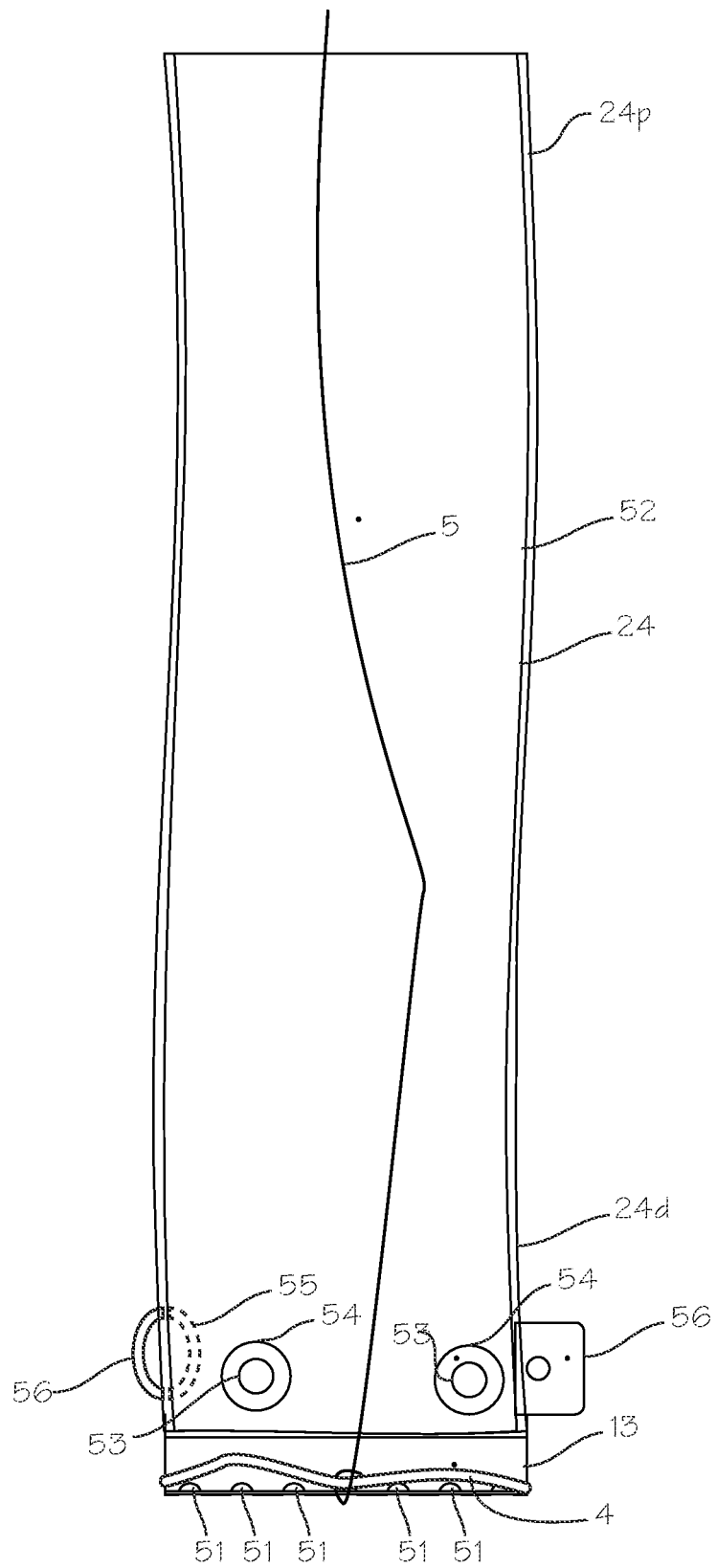
FIG. 39 illustrates various features of the specimen tube which may be used in any of the embodiments disclosed in the previous figures.

FIG. 39 illustrates various features of the specimen tube which may be used in any of the embodiments disclosed in the previous figures. The specimen tube of FIG. 39 includes the main tube 24 and distal skirt 47 with the semi-rigid or resilient hoop 4 secured to the skirt at the distal end 24d of the tube, circumscribing the opening at the distal end, and the tether 5 secured to the hoop and running through the lumen of the tube proximally, and extending from the proximal end 24p of the tube. The hoop is captured in a hem, formed in the skirt, which is modified with the several scalloped cut-outs 51. These cutouts may aid in cinching the distal opening and drawing and everting the cinched hem into the inside of the tube. The tube is constructed of two flat rectangular pieces of plastic, secured to each other along welded seams 52. The hem in this device comprises a plastic film of reduced thickness, compared to the main tube, to facilitate cinching and eversion. For example, the main tube 24 may comprise polyurethane at 2.2 mil thickness, while the hem (which comprises a skirt, similar to the skirt of the inflatable embodiments) and distal tip comprise polyurethane at 1.2 mil thickness. The additional thickness of the main tube may be uniform around the circumference of the tube, or non-uniform, in which case one or more longitudinal stays, formed integrally with the remainder of the main tube but with a thicker wall thickness, will serve to stiffen the main tube relative to the skirt or hem at the distal end of the device. (Thus, several means for stiffening the main tube relative to the skirt include the extra wall thickness described here, the inflatable channels described in relation to FIG. 29, and the stay described in relation to FIG. 21.)

Referring again to FIG. 39, one or more apertures 53, which may be reinforced by grommets 54 provide a reinforced grasping feature, which may be grasped by graspers from within the tube to help push the tube through a cannula and adjust the tube during use. Various other grasping features may be used, including a pocket, a small loop, or a flap or tab 55 on the inside of the tube, or an area of thicker material which may be grasped without risk of tearing, while not occupying much of the tube area to significantly affect eversion. Grasping features may also be added to the exterior of the tube, especially at the distal end, such as grasping tab 56 or grasping loop 57, and these may be used to grasp the tube from the outside, even while disposed within the endoscopic workspace, with graspers introduced into the endoscopic workspace through a separate portal. The apertures 53 may also serve as external grasping features.

The device of FIG. 39 may be inserted into the surgical workspace through a cannula, as described above in relation to the embodiments described in the earlier figures. To insert the distal end of the device into the workspace, the surgeon will grasp the internal grasping feature (a grommet, pocket, loop or flap) and use the grasper to push the distal end of the tube through a cannula or skin incision into the workspace. After the distal end is disposed in the surgical workspace, the surgeon using the device to retrieve a specimen may use a grasper to grasp the internal grasping feature to adjust the tube as necessary. Also, the surgeon may insert a grasper into the workspace through an additional portal, approach the tube from outside the tube, and grasp the external grasping feature (the tab, or the grommet, or a loop or flap) to manipulate the tube, for example, to hold the tube up and open while using another grasper to grasp a specimen and deposit it into the interior of the tube. After depositing the specimen in the tube, the surgeon can again grasp the internal grasping feature or the external grasping feature and manipulate the tube to facilitate eversion while pulling proximally on the tether to evert the skirt portion of the tube into the main portion of the tube, and fully evert the tube.

Various structures for accomplishing beneficial functions can be interchanged while obtaining the benefit of various inventive aspects of the various embodiments disclosed above. The benefits of the everting tube as a means for isolating and withdrawing a specimen can be achieved with the several means for holding the distal end of the specimen tube assembly open, including the semi-rigid hoop of FIG. 1, the semi-rigid tube of FIGS. 21 through 24, the grasper of FIG. 26, or the inflatable channels of FIGS. 29 and 31. The benefits of the everting tube as a means for isolating and withdrawing a specimen can be achieved with the several means for everting the tube, including the hoop and tether combination of FIG. 1, the grasper of FIG. 26, and the loose, flexible suture of FIGS. 29 and 31.

The specimen retrieval system is described above in various embodiments may comprise the tube and a tether fixed to the distal end of the tube, with the tether extending from the distal end of the tube, proximally through the tube, and extending out the proximal end of the tube. The specimen retrieval system may instead comprise the tube and a grasper operable to grasp the distal end of the tube, with the grasper extending from the distal end of the tube, proximally through the tube, and extending out the proximal end of the tube where the handle may be operated by the surgeon to grasp the distal edge of the tube. Each of the embodiments may also include a hoop fixed to the tube at its distal end, in a casing or otherwise, or may include inflatable channels extending lengthwise along the tube, to serve as a means of holding the distal end of the tube open, at least partially, while a specimen is deposited within the tube.

The several methods described above may be broadly described as a method of retrieving a tissue specimen from an endoscopic workspace in the body of a patient with the steps of inserting a tube through an opening to the workspace, and into the endoscopic workspace, so that a distal end of the tube is disposed in the workspace and a proximal end of the tube is disposed outside the workspace, placing the tissue specimen inside the tube and everting the distal end of the tube by drawing the distal end of the tube inside the remainder of the tube and pulling said distal end proximally within the tube, to isolate the specimen from the workspace, and then pulling the tube, after everting the distal end, through the opening, to remove the specimen and the tube from the workspace. The benefits of the method of removing a specimen within a surgical workspace by drawing it into a tube, everting or partially everting the tube to capture the specimen between an everted portion of the tube and an un-everted portion of the tube, and then withdrawing the everted tube from the surgical workspace can be achieved with any of the disclosed means for everting the tube, and any of the means for holding the tube open so that it may receive the specimen.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A specimen retrieval system comprising:
a tube having a distal end and a proximal end, said distal end being open, said tube having a lumen extending from the distal end to the proximal end;
a tether comprising a limp thread or suture fixed to the distal end of the tube, said tether extending from the distal end of the tube and extending out the proximal end of the tube, said tether operable to pull the distal end of the tube into an everted configuration relative to the remainder of the tube while the distal end of the tube is in an open configuration.

2. The specimen retrieval system of claim 1 further comprising:
means for holding the distal end of the tube in the open configuration.

3. The specimen retrieval system of claim 2, wherein the means for holding the distal end of the tube in the open configuration comprise a semi-rigid hoop secured to a distal edge of the tube.

4. The specimen retrieval system of claim 3, wherein the tether is fixed to the distal end of the tube through the hoop.

5. The specimen retrieval system of claim 2, wherein the means for holding the distal end of the tube in the open configuration comprise a grasper extending through the tube, from the proximal end of the tube to the distal end of the tube.

6. The specimen retrieval system of claim 2, wherein the means for holding the distal end of the tube in the open configuration comprise one or more inflatable channels extending longitudinally along the tube.

7. The specimen retrieval system of claim 6 wherein:
one inflatable channel is separated from a second, adjacent inflatable channel by a circumferentially extending region of the tube which is not inflatable.

8. The specimen retrieval system of claim 6 wherein:
the one or more inflatable channels terminate at a point proximal to the distal end of the tube, thereby defining a skirt at the distal end of the tube un-supported by the one or more inflatable channels.

9. The specimen retrieval system of claim 6 wherein:
the tube comprises a tube distal portion and a tube proximal portion, and the tube distal portion is isodiametric, and the one or more inflatable channels are dispersed about the circumference of the tube, and terminate at a point proximal to the distal end of the tube, thereby defining a skirt at the distal end of the tube un-supported by the one or more inflatable channels.

10. The specimen retrieval system of claim 6 wherein:
the tube comprises a tube distal portion and a tube proximal portion, and the tube distal portion is isodiametric, 10 to 14 inches long, and 4 to 6 inches wide when un-inflated and laid flat, and the one or more inflatable channels are ½ to 2 inches wide, dispersed about the circumference of the tube, and terminate at a point proximal to the distal end of the tube, thereby defining a skirt at the distal end of the tube un-supported by the one or more inflatable channels.

11. The specimen retrieval system of claim 6 wherein:
the tube comprises a first, outer tube and a second, inner tube, and the inner tube is secured to the outer tube to create a plurality of inflatable chambers separated by un-inflatable regions.

12. The specimen retrieval system of claim 11 wherein the first tube comprises a nylon film, coated with urethane, and coated with silicon, and the first tube and the second tube are heat sealed together.

13. The specimen retrieval system of claim 6 further comprising:
an aperture in each inflatable channel, said aperture sized and dimensioned to allow fluid in each inflatable channel to leak from each inflatable channel at a rate lower than the rate at which each inflatable channel is inflated.

14. The specimen retrieval system of claim 6 further comprising a manifold in fluid communication with each of the one or more inflatable channels.

15. The specimen retrieval system of claim 1 further comprising:
a casing disposed near the distal end of the tube; wherein a first portion of the tether runs through the casing.

16. The specimen retrieval system of claim 1 further comprising:
a plurality of inflatable channels disposed within a wall of the tube, said inflatable channels oriented longitudinally along the tube.

17. The specimen retrieval system of claim 1 further comprising:
a rod having a blunt rounded distal tip.

18. The specimen retrieval system of claim 17 further comprising:
a semi-rigid guide ring located on a distal end of the rod wherein a proximal end of the rod extends out of the proximal end of the tube.

19. The specimen retrieval system of claim 18 wherein, the guide ring is resiliently deformable and operable to be compressed to a small configuration.

20. The specimen retrieval system of claim 1 wherein, the distal end of tube is folded to the inside of the tube to form an everted cuff.

21. The specimen retrieval system of claim 1 where the tether is disposed in the lumen of the tube and is fixed to the distal end of the tube in a configuration in which the tether is further operable, when pulling the tether proximally, to pull the distal end of the tube proximally into the lumen while the distal end of the tube is in the open configuration.

* * * * *